United States Patent
Rodriguez Fernandez et al.

(10) Patent No.: US 8,367,620 B2
(45) Date of Patent: Feb. 5, 2013

(54) PEPTIDIC GROWTH HORMONE SECRETAGOGUES ANALOG COMPOUNDS AND PREPARATIONS THEREOF

(75) Inventors: Rolando Eduardo Rodriguez Fernandez, Ciudad de la Habana (CU); Ania De La Nuez Veulens, Ciudad de la Habana (CU); Mario Pablo Estrada Garcia, Ciudad de la Habana (CU); Rebeca Martinez Rodriguez, Ciudad de la Habana (CU); Glay Chinea Santiago, Ciudad de la Habana (CU); Osvaldo Reyes Acosta, Ciudad de la Habana (CU); Julio Raul Fernandez Masso, Ciudad de la Habana (CU); Diana Garcia del Barco Herrera, Ciudad de la Habana (CU); Jorge Amador Berlanga Acosta, Ciudad de la Habana (CU); Alexis Musacchio Lasa, La Habana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 734 days.

(21) Appl. No.: 12/281,085

(22) PCT Filed: Feb. 28, 2007

(86) PCT No.: PCT/CU2007/000007
§ 371 (c)(1),
(2), (4) Date: Nov. 19, 2009

(87) PCT Pub. No.: WO2007/098716
PCT Pub. Date: Sep. 7, 2007

(65) Prior Publication Data
US 2010/0055118 A1 Mar. 4, 2010

(30) Foreign Application Priority Data

Feb. 28, 2006 (CU) .................................. 2006-0050

(51) Int. Cl.
*C07K 7/06* (2006.01)
*C07K 7/08* (2006.01)
(52) U.S. Cl. ........ 514/21.6; 514/21.5; 530/328; 530/329
(58) Field of Classification Search ........................ None
See application file for complete search history.

(56) References Cited

U.S. PATENT DOCUMENTS

| 5,100,669 | A | 3/1992 | Hyon et al. |
| 6,086,863 | A | 7/2000 | Ritter et al. |
| 7,465,704 | B2 | 12/2008 | Berlanga Acosta et al. |

OTHER PUBLICATIONS

Cort JH, et al., "Regional and Systemic Haemodynamic Effects of Some Vasopressins: Structural Features of the Hormone which Prolong Activity", Europ. J. Clin. Invest, vol. 5, 1975, pp. 165-175, XP009084677, Figure 1.
Lammek B et al., "Synthesis of three NH2-terminally extended arginine-vasopressins with prolonged biological activities", Experentia, vol. 43, 1987, pp. 1211-1212, XP009084729, Table 2.

*Primary Examiner* — Anish Gupta
(74) *Attorney, Agent, or Firm* — Hoffmann & Baron, LLP

(57) ABSTRACT

Peptidic chemical compounds obtained by in silico molecular modelling, having a structure that enables them to perform the same functions of peptidic growth hormone secretagogues. The invention also comprises the preparations containing such compounds and the use in medicines, food additives, nutritional supplements or other formulations of human or animal use.

4 Claims, 8 Drawing Sheets

PEPTIDIC GROWTH HORMONE SECRETAGOGUES ANALOG COMPOUNDS AND PREPARATIONS THEREOF

CROSS-REFERENCE TO RELATED APPLICATION

This application is a National Phase application of International Application No. PCT/CU2007/000007 filed Feb. 28, 2007, which asserts priority to Cuban Application No. CU 2006/0050 filed on Feb. 28, 2006. The foregoing applications are hereby incorporated by reference in their entirety herein.

TECHNICAL FIELD

The present invention can be described in the field of rational design of biologically active molecular entities regulating the metabolic activity and cytoprotection of the organisms. More specifically on compounds analog to peptidic growth hormone secretagogues whose activity includes but it is not restricted to: the controlled release of growth hormone, cardioprotection, the increase of the functional response of the cardiovascular system, neuroprotection, appetite regulation and control, fat intake and energetic metabolism.

PREVIOUS ART

The synthetic growth hormone (GH) secretagogues consist of a family of ligands including peptidic and non peptidic molecules, being first described by Momany and Bowers before the isolation of GH releasing hormone (GHRH) synthetic peptides of 6 and 7 amino acids resulting into potent GH releasing peptides (GHRPs); such peptides were described prior to the knowledge of its function in the organism or their way of action. Mutational studies and in vivo and in vitro experiments revealed that the two amino acid arrangement L-D and D-L separated by one amino acid acting as spacer, was considered optimal for the GH releasing activity, and peptide(His-D-Trp-Ala-D-Trp-Phe-NH2) was conformed releasing GH at a concentration of 10 to 30 ng/mL reaching to a peptide known as GHRP-6 (His-D-Trp-Ala-Trp-D-Phe-Lys-NH2) where the Lys residue was needed only to improve the in vivo activity because it was not deemed as functional in vitro (Momany F. A., Bowers C. Y., et. al. (1981) Design, synthesis and biological activity of peptides which release growth hormone, in vitro. *Endocrinology*, 108:31-39).

Other analog peptides were discovered; in 1993 Bowers et al. discovered two GHRP-6analog peptides, el GHRP-2 (D-Ala-D-β-Nal-Ala-Trp-D-Phe-Lys-NH2) y el GHRP-1 (Ala-His-D-β-Nal-Ala-Trp-D-Phe-Lys-NH2). These three secretagogues showed an increased GH release in vitro from incubated hypothalamus-pituitary than that from the pituitary gland alone, demonstrating that the hypothalamic impulse was important in such action. Also it was demonstrated, even in humans, that the synergistic action of GHRP and GHRH released more GH than any of the two by itself (Bowers C. Y. (1993) GH-releasing peptides: structure and kinetics. *J Pediatr Endocrinol*, 6(1):21-31).

From the peptide known as GHRP-2 new cyclic peptides were created by substituting N-terminal D-Ala with an amino acid having the side chain linked to another amino acid inserted between D-Phe and Lys. One of such peptides (D-Lys-D-β-Nal-Ala-Trp -D-Phe-Glu-Lys-NH2) resulted in a 10 fold increased activity in vitro and a comparable efficacy in vivo to GHRP-6 (McDowell R. S., et al. (1995) Growth hormone secretagogues: characterization, efficacy, and minimal bioactive conformation. *PNAS USA*, 92(24):11165-11169). The experiments were completed with structural studies in solution of the DL cyclic peptides reaching to the conclusion that the introduction of D amino acids in the peptidic compounds was essentially needed to elicit the desired activity. Other investigations were directed to find active molecules with an increased oral bioavailability and longer clearance times, yielding the discoveries of new GHRPs and other non peptidic molecules. In 1993, the first non peptidic GH secretagogue was described (Smith R. G., et al. (1993) A nonpeptidyl growth hormone secretagogue, *Science*, 260:1640-43), and later is described in the synthesis of a non peptidic and more potent GHS, MK-0677, having a high bioavailability and able to stimulate GH secretion 24 h after a single dose oral administration (Patchett A. A., Nargund R.P., et al. (1995) Design and biological activities of L-163,191 (MK-0677): a potent, orally active growth hormone secretagogue. *PNAS USA*, 92:7001-7005; Smith R. G., Van der Ploeg L. H., et al. (1997) Peptidomimetic regulation of growth hormone secretion. *Endocr. Rev*, 18:621-645). More recently another peptidomimetic GHS was designed with a selective and potent GH releasing activity (EP1572) showing a GH secretagogue receptor (GHS-R) binding potency in human and animal tissues similar to that of ghrelin and peptidic GHS inducing a marked increase in GH after the subcutaneous administration to newborn rats (Broglio F., Boutignon F., et al. (2002) EP1572: a novel peptido-mimetic GH secretagogue with potent and selective GH-releasing activity in man. *J Endocrinol Invest*, 25:RC26-RC28).

In 1999 ghrelin was discovered as a 28 amino acid peptide produced mainly in the stomach, however its mARN has also been found in several other tissues. It is produced in the stomach by the X/A cells which are the major population of endocrine cells in the oxintic mucosa. Ghrelin is also found in the hypothalamic arcuate nucleus where its RNA is present in NPY and AGRP neurons, involved in appetite control and the energetic balance (Kojima M., Hosoda H., et al. (1999) Ghrelin is a growth-hormone-releasing acylated peptide from stomach. *Nature*, 402:656-60; Nakazato M., Murakami N., et al. (2001) A role for ghrelin in the central regulation of feeding. *Nature*, 409:194-198). Its RNA has been also localized in pancreas and intestine. It circulates in the bloodstream of adult humans in a concentration of 100-120 fmol/ml, suggesting that is secreted by the stomach cells and it may act by an endocrine pathway. The production of ghrelin has been also reported in neoplastic tissues (Takaya K., Ariyasu H., et al. (2000) Ghrelin strongly stimulates growth hormone release in humans. *J. Clin. Endocrinol. Metab*, 85:4908-11; Papotti M., et al. (2001) Substantial production of ghrelin by a human medullary thyroid carcinoma cell line. *J Clin Endoc. Metab*, 86:4984-4990).

Other animal studies showed that the secretion of ghrelin is pulsatile and more associated to appetite to the GH pulses (Tolle V., Bassant M. H., et al. (2002) Ultradian rhythmicity of ghrelin secretion in relation with GH, feeding behaviour, and sleep wake patterns in rats. *Endocrinology*, 143:1353-1361).

Ghrelin is the first natural hormone being found with a hydroxyl group of one of the serines acylated with octanoic acid. This modification has being described as essential for the binding to GHS-R1a, as well as for the GH releasing capacity, and probably to other endocrine actions.

Non acylated ghrelin circulates in major amounts than the acylated. Although it was not described as direct endocrine action it is regarded as acting in other non-endocrine functions like cardiovascular effects, cardioprotective, antiproliferatives, and cytoprotecting in general, probably mediated by the binding to other subtypes of GHS-R (Matsumoto M., Hosoda H., et al. (2001) Structure-activity relationship of ghrelin: pharmacological study of ghrelin peptides. *Biochem Biophys Res Commun,* 287:142-146; Hosoda H., Kojima M., et al. (2000) Ghrelin and des-acyl ghrelin: two major forms of rat ghrelin peptide in gastrointestinal tissue. *Biochem Biophys Res Commun,* 279:909-913; Cassoni P., Papotti M., et al. (2001) Identification, characterization, and biological activity of specific receptors for natural (ghrelin) and synthetic growth hormone secretagogues and analogs in human breast carcinomas and cell lines. *J Clin Endocrinol Metab,* 86:1738-1745).

There is another endogenous Ligand for GHS-R1a that can be isolated from the stomach endocrine mucosa, des-Gln14-ghrelin as the result of an alternative processing of the ghrelin gene losing Gln14 and as ghrelin it does experiment the same acylation process on Ser3.

Studies made with several ghrelin analogs having the third residue modified with several aliphatic or aromatic groups and several short peptides derived from the ghrelin side chain showed that the hydrophobic groups in residue 3 are essential to the activity. Also has been observed the short segments containing the first five residues of ghrelin are capable of activating the receptor with a comparable efficiency to the whole peptide. Tetra peptides were shown to be less potent and fragments lacking the N-Terminal were unable to activate the receptor (Bednarek M. A., Feighner S. D., et al. (2000) Structure-Function Studies on the New Growth Hormone-Releasing Peptide, Ghrelin: Minimal Sequence of Ghrelin Necessary for Activation of Growth Hormone Secretagogue Receptor 1a. *J Med Chem,* 43: 4370-4376; Silva Elipe M. V., Bednarek M. A., et al. (2001) 1H NMR structural analysis of human ghrelin and its six truncated analogs. *Biopolymers,* 59:489-501). Such studies suggested that the complete ghrelin sequence is not essential for the activity and Gly-Ser-Ser (n-octanoyl)-Phe is the active fragment in the activity as agonist of GHS-R1a.

Before and after the discovery of ghrelin, a great effort was made to find small molecules and derivatives that can be ligands of the GHS-R. An important number of patents described molecules of such type (U.S. Pat. Nos. 3,239,345; 4,036,979; 4,411,890; 5,492,916; 5,494,919; 5,559,128; 5,663,171; 5,721,250; 5,721,251; 5,723,616; 5,726,319; 5,767,124; 5,798,337; 5,830,433; 5,919,777; 6,034,216; 6,548,501; 6,559,150; 6,576,686; 6,686,359; Intl Pats: WO 89/07110; 89/07111; 92/07578; 93/04081; 94/11012; 94/13696; 94/19367; 95/11029; 95/13069; 95/14666; 95/17422; 95/17423; 95/34311; 96/02530; 96/15148; 96/22996; 96/22997; 96/24580; 96/24587; 96/32943; 96/33189; 96/35713; 96/38471; 97/00894; 97/06803; 97/07117; 97/09060; 97/11697; 97/15191; 97/15573; 97/21730; 97/22004; 97/22367; 97/22620; 97/23508; 97/24369; 97/34604; 97/36873; 97/38709; 97/40023; 97/40071; 97/41878; 97/41879; 97/43278; 97/44042; 97/46252; 98/03473; 98/10653; 98/18815; 98/22124; 98/46569; 98/51687; 98/58947; 98/58948; 98/58949; 98/58950; 99/08697; 99/09991; 99/36431; 99/39730; 99/45029; 99/58501; 99/64456; 99/65486, 99/65488; 00/01726; 00/10975; 01/47558; 01/92292; 01/96300; 01/97831) (Carpino, P. (2002) Recent developments in ghrelin receptor (GHS-. Rla) agonists and antagonists *Exp. Opin. Ther. Patents* 12:1599-1618). After such extensive revision other compounds have been described as antagonists of the GHS-R (US2005288316 and W02005048916) and others described as also binding to GHS-R and used with various purposes. (W02005046682; W02005039625; JP2003335752; US2004009984; US2003130284; W003004518) More recently a new series of macro cyclic compounds was added to the set with the main purpose of being agonists of GHS-R without eliciting the release of GH (US2006025566).

GHS-R is a class A G-coupled protein receptor, expressed by a single gene in the chromosomal 3q26.2 locus in humans. Two types of cDNA were identified result of the alternative processing of the pre-mRNA (McKee K. K., Tan C. P., et al. (1997) Cloning and characterization of two human G protein-coupled receptor genes (GPR38 and GPR39) related to the growth hormone secretagogue and neurotensin receptors. *Genomics,* 46:426-434; McKee K. K., Palyha O. C., et al. (1997) Molecular analysis of rat pituitary and hypothalamic growth hormone secretagogue receptors. *Mol Endocrinol,* 11:415-423; U.S. Pat. No. 6,242,199; WO 97/21730). cDNA 1a encode a 366 amino acid receptor with seven transmembrane segments (GHS-R1a). cDNA 1b encodes a shorter protein (GHS-R1b) having 289 amino acids and five transmembrane segments. Although the role of GHS-R1b is yet unknown, it has been proved the expression in several endocrine and non-endocrine tissue (Howard A. D., Feighner S. D., et al. (1996) A receptor in pituitary and hypothalamus that functions in growth hormone release. *Science,* 273:974-977; Gnanapavan S., Kola B., et al. (2002) The tissue distribution of the mRNA of ghrelin and subtypes of its receptor, GHS-R, in humans. *J Clin Endocrinol Metab.* 87:2988; Smith R. G., Leonard R., et al. (2001) Growth hormone secretagogue receptor family members and ligands. *Endocrine,* 14:9-14).

The human GHS-R1a has a 96 and 93% identity with those of the rat and swine respectively, and a close relation has been shown between the sequence of human GHS-R1a and those of telosteous fish. Such findings suggest that GHS-R1a is highly conserved between species and probably exert an essential biological function. (Palyha O. C., Feighner S. D., et al. (2000) Ligand activation domain of human orphan growth hormone (GH) secretagogue receptor (GHS-R) conserved from pufferfish to humans. *Mol Endocrinol.* 14:160-169).

The binding of ghrelin and synthetic GHS to GHS-R1a activates the phospholipase C signalling pathway, increasing the concentration of inositol-1,4,5 triphosphate (IP3), and protein kinase C(PKS) activation, followed by the release of $Ca^{2+}$ from the intracellular stores. The activation of GHS-R also inhibits the $K^+$ channels allowing the intake of $Ca^{2+}$ through L type voltage gated channels but not of type T. Differently to GHS-R1a, GHS-R1b does not bind or responds to GHS and its function is yet unknown. (Chen C., Wu D., et al. (1996) Signal transduction systems employed by synthetic GH-releasing peptides in somatotrophs. *J Endocrinol.* 148: 381-386; Casanueva F. F., Dieguez C. (1999) Neuroendocrine regulation and actions of leptin. *Front Neuroendocrinol,* 20:317-363; Howard A. D., Feighner S. D., et al. (1996) A receptor in pituitary and hypothalamus that functions in growth hormone release. *Science,* 273:974-977).

Synthetic GHS, ghrelin and its natural isoform (des-Gln14-ghrelin) bind with high affinity to GHS-R1a, and the efficiency on displacing membrane bound [$^{35}$S] MK-0677 or [$^{125}$I] [Tyr$^4$]ghrelin is correlated to the concentration required to stimulate GH release (Muccioli G., Papotti M., et al. (2001) Binding of 125I-labeled ghrelin to membranes from human hypothalamus and pituitary gland. *J Endocrinol Invest.* 24:RC7-RC9; Hosoda H., Kojima M., et al. (2000) Purification and characterization of rat des-Gln14-ghrelin, a second endogenous ligand for the growth hormone secretagogue receptor. *J Biol Chem,* 275:21995-22000).

To determine the essential structural characteristics of ghrelin for the binding and activation of GHS-R1a, short ghrelin peptides were studied in HEK-293 cells, expressing human GHS-R1a observing that 4 and 5 amino acid ghrelin N-terminal peptides were able to activate the receptor. Based on this in vitro results it is postulated that Gly-Ser-Ser(n-octanoyl)-Phe is essentially required for the activation of the receptor (Van der Lely A. J., Tschop M., et al. (2004) Biological, Physiological, Pathophysiological, and Pharmacological Aspects of Ghrelin. *Endocrine Reviews,* 25(3):426-457). The first 7 amino acid of ghrelin are conserved among all studied species, however the ability of ghrelin derivatives to activate GHS-R1a in transfected cells does not seems an indication for the capacity to stimulate GH release in somatotroph cells, recently it was shown that (1-4) and (1-8) octanoyl ghrelin are not able to stimulate the release of GH in rats and were not effective displacing [$^{125}$I] [Tyr$^4$] ghrelin from the binding site in preparations of human pituitary or hypothalamic membranes (Torsello A., Ghe C., et. al. (2002) Short ghrelin peptides neither displace ghrelin binding in vitro nor stimulate GH release in vivo. *Endocrinology,* 143: 1968-1971). Other study on the same cells expressing human or swine GHS-R1a it was found that adenosine also activates the receptor, but like the short ghrelin analogs can not stimulate the GH secretion, suggesting that adenosine is a partial agonist of GHS-R1a bound to a different site in the receptor that MK-0677 or GHRP-6 (Smith R. G., Griffin P. R., et. al. (2000) Adenosine: a partial agonist of the growth hormone secretagogue receptor. *Biochem Biophys Res Commun,* 276: 1306-1313). More recently has been reported that GHS-R1a can also bind cortistatin (CST), a somatostatin (SS) homolog neuropeptide not being able by itself to recognize GHS-R1a (Deghenghi R., Papotti M., et. al. (2001) Cortistatin, but not somatostatin, binds to growth hormone secretagogue (GHS) receptors of human pituitary gland. *J Endocrinol Invest,* 24:RC1-RC3). GHS-R1a is expressed in the arcuate nucleus and pituitary somatotroph cells, crucial zones for neuroendocrine and appetite stimulation activities of ghrelin and synthetic GHS. (Willesen M. G., Kristensen P., Romer J. (1999) Co-localization of growth hormone secretagogue receptor and NPY mRNA in the arcuate nucleus of the rat. *Neuroendocrinology,* 70:306-316; Bluet-Pajot M. T., Tolle V., et. al. (2001) Growth hormone secretagogues and hypothalamic networks. *Endocrine,* 4:1-8; Shintani M., Ogawa Y., et. al. (2001) Ghrelin, an endogenous growth hormone secretagogue, is a novel orexigenic peptide that antagonizes leptin action through the activation of hypothalamic neuropeptide Y/Y1 receptor pathway. *Diabetes,* 50:227-232). Ghrelin and synthetic GHS, stimulate the expression of neuronal activity markers (c-fos and EGR-1) in neurons of the arcuate nucleus an GHS-R1a mRNA has been detected in extra hypothalamic areas like the dented twist and regions CA2 and CA3 on the hippocampus, substance nigra pars compacta, and ventral tegmental area, dorsal and medial Raphe nuclei, Edinger-Westphal nucleus, bridge and spinal bulb, indicating possible extra hypothalamic actions. mRNA has been also found on several peripheral organs like stomach, intestine, pancreas, kidney, heart, aorta, several human adenomas and some human lung, stomach and pancreas neoplasm. (Hewson A. K., Dickson S. L. (2000) Systemic administration of ghrelin induces Fos and Egr-1 proteins in the hypothalamic arcuate nucleus of fasted and fed rats. *J Neuroendocrinol,* 12:1047-1049; Muccioli G., Ghe et. al. (1998) Specific receptors for synthetic GH secretagogues in the human brain and pituitary gland. *J Endocrinol,* 157:99-106; Guan X. M., Yu H., et. al. (1997) Distribution of mRNA encoding the growth hormone secretagogue receptor in brain and peripheral tissues. *Brain Res Mol Brain Res,* 48:23-29; Mori K., Yoshimoto et. al. (2000) Kidney produces a novel acylated peptide, ghrelin. *FEBS Lett,* 486:213-216; Nagaya N., Miyatake K., et. al. (2001) Hemodynamic, renal, and hormonal effects of ghrelin infusion in patients with chronic heart failure. *J Clin Endocrinol Metab,* 86:5854-5859; Korbonits M., Bustin S. A., et. al. (2001) The expression of the growth hormone secretagogue receptor ligand ghrelin in normal and abnormal human pituitary and other neuroendocrine tumours. *J Clin Endocrinol Metab,* 86:881-887; Papotti M., Cassoni P., et. al. (2001) Ghrelin-producing endocrine tumors of the stomach and intestine. *J Clin Endocrinol Metab,* 86:5052-5059).

Ghrelin and GHS have a high affinity to GHS-R1a. However there are evidences of other additional sites for GHS. Specific sites for Tyr-Ala-hexarelin and other GHS with a similar receptor density at least equal to the density found in pituitary has been found in human and rat heart and many other non endocrine peripheral tissues like: lungs, arteries, skeletal muscles, kidney, and liver (Muccioli G., Ghe C., et. al. (1998) Specific receptors for synthetic GH secretagogues in the human brain and pituitary gland. *J Endocrinol,* 157:99-106; Muccioli G., Broglio F., et. al. (2000) Growth hormone-releasing peptides and the cardiovascular system. *Ann Endocrinol (Paris),* 61:27-31; Bodart V., Bouchard J. F., et. al. (1999) Identification and characterization of a new growth hormone-releasing peptide receptor in the heart. *Circ Res,* 85:796-802; Katugampola S., Davenport A. (2003) Emerging roles for orphan G protein-coupled receptors in the cardiovascular system. *Trends Pharmacol Sci,* 24:30-35; Ghigo E., Arvat E., et. al. (2001) Biologic activities of growth hormone secretagogues in humans. *Endocrine,* 14:87-93; Papotti M., Ghe C., Cassoni P., et. al. (2000) Growth hormone secretagogue binding sites in peripheral human tissues. *J Clin Endocrinol Metab,* 85:3803-3807). Such binding sites showed low affinity for ghrelin and are probably not ghrelin receptors but peptide ghrelin analog receptors. Heart GHS-R has a higher (84 kDa) molecular weight than GHS-R1a and no sequence homology, the predicted amino acid sequence for the receptor in the heart is similar to CD36 (Papotti M., Ghe C., et. al. (2000) Growth hormone secretagogue binding sites in peripheral human tissues. *J Clin Endocrinol Metab,* 85:3803-3807; Bodart V., Febbraio M., et. al. (2002) CD36 mediates the cardiovascular action of growth hormone-releasing peptides in the heart. *Circ Res,* 90:844-849). The functional meaning of peripheral tissue GHS receptors and findings in the cardiovascular system suggest that such binding sites modulate the cardioprotective activities of peptidic GHS.

Ghrelin and other synthetic secretagogues stimulate the release of GH by the somatotroph cells in vitro probably by membrane depolarization and by the increment of the GH secreted per cell, reporting also a stimulatory effect of GHS on the GH synthesis. (Kojima M., Hosoda H., et. al. (1999) Ghrelin is a growth-hormone-releasing acylated peptide from stomach. *Nature,* 402:656-660; Sartor O., Bowers C. Y., Chang D. (1985) Parallel studies of His-DTrp-Ala -Trp-DPhe-Lys-NH2 and human pancreatic growth hormone releasing factor-44-NH2 in rat primary pituitary cell monolayer culture. *Endocrinology,* 116:952-957; Bowers C. Y., Sartor A. O., et. al. (1991) On the actions of the growth hormone-releasing hexapeptide, GHRP. *Endocrinology,* 128: 2027-2035; Wu D., Chen C., et al. (1994) The effect of GH-releasing peptide-2 (GHRP-2 or KP 102) on GH secretion from primary cultured ovine pituitary cells can be abolished by a specific GH-releasing factor (GRF) receptor antagonist. *J Endocrinol,* 140:R9-R13;).

Early studies showed GHS stimulating the GH secretion using a different receptor and pathway. An antagonist of the GHRH receptor inhibits the GHRH elicited GH secretion, but not the release of GHRH stimulated by secretagogues. An alleged GHS-R antagonist does not affect the GH release in response to GHRH. GHRP-6 does not compete with GHRH in receptor binding assays for GHRH binding sites. There is an additive effect on the GH release upon the co administration of GHS and GHRH, and there is no crossed desensitation between GHRH and GHS in terms of GH release. (Wu D., Chen C., et al. (1994) The effect of GH-releasing peptide-2 (GHRP-2 or KP102) on GH secretion from primary cultured ovine pituitary cells can be abolished by a specific GH-releasing factor (GRF) receptor antagonist. *J Endocrinol*, 140: R9-13; Thorner M. O., Hartman M. L., et al. (1994) Current status of therapy with growth hormone-releasing neuropeptides. Savage MO, Bourguignon J, Grossman A B (eds). *Frontiers in Pediatric Neuroendocrinology*, 161-167).

The GH releasing activity of GHS is larger in pituitary-hypothalamus preparations than in isolated pituitary, in agreement with the evidence of the larger in vivo GH stimulating effects. (Mazza E., Ghigo E., et. al. (1989) Effect of the potentiation of cholinergic activity on the variability in individual GH response to GH-releasing hormone. *J Endocrinol Invest*, 12:795-798; Bowers C. Y., Sartor A. O., et. al. (1991) On the actions of the growth hormone-releasing hexapeptide, GHRP. *Endocrinology*, 128:2027-2035; Clark R. G., Carlsson M. S., et. al. (1989) The effects of a growth hormone-releasing peptide and growth hormone releasing factor in conscious and anaesthetized rats. *J Neuroendocrinol*, 1:249-255).

On the hypothalamic level, ghrelin and GHS act upon the GHRH secretor neurons and incremented levels of GHRH has been observed in the pituitary portal circulation after the administration of GHS in sheep. (Conley L. K., Teik J. A., et. al. (1995) Mechanism of action of hexarelin and GHRP-6: analysis of the involvement of GHRH and somatostatin in the rat. *Neuroendocrinology*, 61:44-50; Guillaume V., Magnan E., et. al. (1994) Growth hormone (GH)-releasing hormone secretion is stimulated by a new GH-releasing hexapeptide in sheep. *Endocrinology*, 135:1073-1076).

GHS requires of GHRH to fully express its GH releasing effect, in humans the GH response is inhibited by GHRH receptor antagonists, and by pituitary-hypothalamic disconnection. (Bluet-Pajot M. T., Tolle V., et al. (2001) Growth hormone secretagogues and hypothalamic networks. *Endocrine*, 14:1-8; 148:371-380; Popovic V., Miljic D., et al. (2003) Ghrelin main action on the regulation of growth hormone release is exerted at hypothalamic level. *J Clin Endocrinol Metab*, 88:3450-3453). Patients with a deficiency on the GHRH receptor do not show an increase in GH secretion as a response to GHS stimulation but keep the capacity to increase the cortisol, ACTH and PRL after the GHS stimulation. (Maheshwari H. G., Pezzoli S. S., et al. (2002) Pulsatile growth hormone secretion persists in genetic growth hormone-releasing hormone resistance. *Am J Physiol Endocrinol Metab*, 282:E943-E951; Maheshwari H. G., Rahim A., et al. (1999) Selective lack of growth hormone (GH) response to the GH-releasing peptide hexarelin in patients with GH-releasing hormone receptor deficiency. *J Clin Endocrinol Metab*, 84:956-959; Gondo R. G., Aguiar-Oliveira M. H., Hayashida C. Y., et al. (2001) Growth hormone-releasing peptide-2 stimulates GH secretion in GH-deficient patients with mutated GH-releasing hormone receptor. *J Clin Endocrinol Metab*, 86:3279-3283), In animals and humans there is evidence of GHS and GHRH induced homologous but not heterologous desensitation, GHS activity homologous desensitation has been shown during GHS infusion, but not on the intermittent daily oral or nasal administration of the peptide for more than 15 days. (Ghigo E., Arvat E., et al. (1994) Growth hormone-releasing activity of hexarelin, a new synthetic hexapeptide, after intravenous, subcutaneous, intranasal, and oral administration in man. *J Clin Endocrinol Metab*, 78:693-698; Ghigo E., Arvat E., et al. (1996) Short-term administration of intranasal or oral hexarelin, a synthetic hexapeptide, does not desensitize the growth hormone responsiveness in human aging. *Eur J Endocrinol*, 135:407-412). On the other hand the parenteral, intranasal or oral administration of GHS increases the GH spontaneous pulse and raises the IGF-1 levels in young healthy adults, like in children and elderly subjects. (Chapman I. M., Bach M. A., et al. (1996) Stimulation of the growth hormone (GH)-insulin-like growth factor I axis by daily oral administration of a GH secretagogue (MK-677) in healthy elderly subjects. *J Clin Endocrinol Metab*, 81:4249-4257; Copinschi G., Van Onderbergen A., et al. (1996) Effects of a 7-day treatment with a novel, orally active, growth hormone (GH) secretagogue, MK-0677, on 24-hour GH profiles, insulin-like growth factor I, and adrenocortical function in normal young men. *J Clin Endocrinol Metab*, 81:2776-2782; Laron Z., Frenkel J., et al. (1995) Intranasal administration of the GHRP hexarelin accelerates growth in short children. *Clin Endocrinol (Oxf)*, 43:631-635). Ghrelin is capable of stimulating the appetite in rats and this property could be mediates by the syntheses of NPY and AGRP. Intraventricular ghrelin is also capable of nullifying the anorexigenic effects of leptin, and is postulated that there is a competitive interaction between this two peptides on appetite and energy homeostasis control. The circulating concentrations of ghrelin in the rat are augmented upon fasting and are smaller after feeding or glucose ingestion (Shintani M., Ogawa Y., et al. (2001) Ghrelin, an endogenous growth hormone secretagogue, is a novel orexigenic peptide that antagonizes leptin action through the activation of hypothalamic neuropeptide Y/Y1 receptor pathway. *Diabetes*, 50:227-32; Nakazato M., Murakami N., et al. (2001) A role for ghrelin in the central regulation of feeding. *Nature*, 409 (6817):194-198; Tschöp M., Smiley D. L., Heiman M. L. (2000) Ghrelin induces adiposity in rodents. *Nature*, 407: 908-13).

GHS also stimulate appetite and weight gain. Chronic treatment with GHRP-2 stimulate the accumulation of adipose tissue in NPY deficient mice and increase the hypothalamic expression of AGRP mRNA in the controls (Torsello, A., Luoni, M., et al. (1998) Novel hexarelin analogs stimulate feeding in the rat through a mechanism not involving growth hormone release. *Eur. J. Pharmacol*, 360:123-129; Ghigo, E., Arvat, E., et al. (1999) Endocrine and non-endocrine activities of growth hormone secretagogues in humans. *Horm. Res*, 51:9-15; Tschop, M., Statnick, et al. (2002) GH-releasing peptide-2 increases fat mass in mice lacking NPY: indication for a crucial mediating role of hypothalamic agouti-related protein. *Endocrinology*, 143:558-568).

Ghrelin administration to rats yield gain in appetite and weight by a significative increment on the fat tissue without observing changes in the lean mass, bone tissue or growth stimulation. The lipogenic effect of ghrelin is independent of the GH action, and it can be found in a genetically GH deficient rat. GH elicits an increment in the energy expenditure and causes fat elimination, allowing for a balance with ghrelin, ghrelin increases the fat tissue and GH does not allow a decrease in the lean tissue. (Nakazato M., Murakami N., et al. (2001) A role for ghrelin in the central regulation of feeding. *Nature*, 409(6817):194-198; Wren A. M., Small C. J., et al. (2000) The novel hypothalamic peptide ghrelin stimulates food intake and growth hormone secretion. *Endocrinology*, 141(11):4325-4328; Tschop M., Smiley D. L., Heiman M. L. (2000) Ghrelin induces adiposity in rodents. *Nature*, 407: 980-913).

In obese individuals ghrelin levels are depleted and does not decrease after feeding. This is a reversible condition, because weight loss and ghrelin mean plasma levels are incremented. Plasma levels of ghrelin negatively correlate to the body weight index, the body fat weight, the size of the adiposities and the plasma levels of insulin, glucose and leptin (English P. J., Ghatei M. A., et. al. (2002) Food fails to suppress ghrelin levels in obese humans. *J Clin Endocrinol Metab*, 87(6):2984; Tschop M., Weyer C., et. al. (2001) Circulating ghrelin levels are decreased in human obesity. *Diabetes*, 50(4):707-9).

GH insufficiency in obese patients has been reported as reversible after a prolonged diet and a marked weight loss. The chronic increase on the free fatty acids and hyperinsulinism associated with the low ghrelin levels may have an important role causing GH insufficiency in obesity. (Maccario M., Tassone F., Grottoli S., Rossetto R., Gauna C., Ghigo E. (2002) Neuroendocrine and metabolic determinants of the adaptation of GH/IGF-I axis to obesity. *Ann Endocrinol (Paris)*, 63(2 Pt 1):140-144). As ghrelin is being found adipogenic and orexigenic it can be thought on antagonizing it for obesity treatment, however the consequences of such antagonism lower the GH secretion and are associated with the fat mass increase. (Jorgensen J. O., Vahl N., (1996) Influence of growth hormone and androgens on body composition in adults. *Horm Res*, 45:94-98). Long term administration of agonists or antagonists of ghrelin will reveal which of the two effects dominates and determine its influence on the energy balance.

In the obese man the circulating concentrations of ghrelin are diminished and negatively correlated to the body fat tissue and the circulating levels of insulin and leptin (Tschöp M., Weyer C., et. al. (2001) Circulating ghrelin levels are decreased in human obesity. *Diabetes*, 50:707-9).

GH/IGF-I axis has a very important role during cardiac development and for the maintenance of the structure and function or the heart; deterioration on the cardiovascular performance is one of the symptoms of GH deficiency that can be reverted with a GH therapy. (Sacca L, Cittadini A, Fazio S (1994) Growth hormone and the heart. *Endocr Rev* 15:555-573; Caidahl K, Eden S, Bengtsson B Å 1994 Cardiovascular and renal effects of growth hormone. *Clin Endocrinol (Oxf)* 40:393-400).

There are experimental data showing an improvement on the performance of the cardiac muscle due to GH, among them many studies using a myocardial infarction (MI) model in rats, GH treatment after MI resulted in an increment on the systolic ejection volume, cardiac output and other systolic variables, along with a pronounced vasodilation and a lower total peripheral resistance due to GH/IGF-I, probably contributing to improve the myocardial contractility. (Timsit J, Riou B, et al. 1990 Effects of chronic growth hormone hypersecretion on intrinsic contractility, energetics, isomyosin pattern and myosin adenosine triphosphate activity of rat left ventricle. *J Clin Invest* 86:507-515; Tajima M, et al. (1999) Treatment with growth hormone enhances contractile reserve and intracellular calcium transients in myocytes from rats with post infarction heart failure. *Circulation* 99:127-134).

On the other hand, animal models with an excess of GH display a shift to a myosin isoform with a low adenosine triphosphatase activity, they might lower the energy demand on the contraction process. (Timsit J, Riou B, et al. (1990) Effects of chronic growth hormone hypersecretion on intrinsic contractility, energetics, isomyosin pattern and myosin adenosine triphosphate activity of rat left ventricle. *J Clin Invest* 86:507-515).

There are several studies on the cardiac and peripheral effects of GH and/or IGF-I, among them good clinical data pointing to a future role of GH/IGF-I on the cardiovascular therapy. (Fazio S., Sabatini D., et al. (1996) A preliminary study of growth hormone in the treatment of dilated cardiomyopathy. *N Engl J Med*, 334:809-814).

Several synthetic GHS and ghrelin have cardioprotective properties in several in vivo studies improving several cardiac function variables, having a comparable effect with those of GH. The likelihood of hexarelin haemodinamic profile with those of GH could suggest that GHS action is mediated by GH, recent studies however support a direct action on the heart. (Locatelli V., Rossoni G., (1999) Growth Hormone independent cardioprotective effects of hexarelin in the rat. *Endocrinology*, 140:4024-4031; Tivesten Å., Bollano E., (2000) The growth hormone secretagogue hexarelin improves cardiac function in rats after experimental myocardial infarction. *Endocrinology*, 141:60-66).

GHS-R1a mRNA has been found in aorta and heart, and it is also increased in cardiomyocyte cultures after preincubation with hexarelin (Gnanapavan S., Kola B., et al. (2002) The tissue distribution of the mRNA of ghrelin and subtypes of its receptor, GHS-R, in humans. *J Clin Endocrinol Metab*, 87: 2988-2991; Nagoya N., Kojima M., et al. (2001) hemodynamic and hormonal effects of human ghrelin in healthy volunteers. *Am J Physiol Regul Integr Comp Physiol*, 280: R1483-R1487; Pang J.-J., Xu R.-K., et al. (2004) Hexarelin protects rat cardiomyocytes from angiotensin II-induced apoptosis in vitro. *Am J Physiol Heart Circ Physiol*, 286(3): H1063-1069).

Specific ghrelin binding sites have been identified in rat heart and human arteries, where the receptor density is increased by atherosclerosis and radioactively labelled peptidic GHS were found specifically bound to rat myocardial cells and several human cardiovascular tissues (ventricle, auricle, aorta, coronaries, carotid, endocardium and vena cava), in higher amount than to the pituitary (Katugampola S. D. (2001) [125I-His(9)]-ghrelin, a novel radioligand for localising GHS orphan receptors in human and rat tissue: up-regulation of receptors with atherosclerosis. *Br J Pharmacol*, 134:143-149; Ong H., McNicoll N., et al. (1998) Identification of a pituitary growth hormone-releasing peptide (GHRP) receptor subtype by photo affinity labeling. *Endocrinology*, 139:432-435; Bodart V., McNicoll N., et al. (1999) Identification and characterization of a new GHRP receptor in the heart. *Circ Res*, 85:796-808; Papotti M., Ghe C., et al. (2000) Growth hormone secretagogue binding site in periferical human tissues. *J Clin Endocrinol Metab*, 85: 3803-3807).

Even though the administration of high pharmacological doses of peptidic GHS induce a clear but transient vasoconstriction in perfunded rat heart using young rats with induced GH deficiency by immunization with GHRH, it has been also found that hexarelin can protect against the myocardial damage induced by ischemia and reperfusion Such protective activity has been associated to prostacyclin release and the recovery of Angiotensin II vasopressor activity. (Bodart V., Febbario M., et al. (2000) CD36 mediates the cardiovascular action of growth hormone-releasing peptides in the heart. *Circ Res*, 90:844-849; de Gennaro Colonna V., Rossoni G., et al. (1997) Hexarelin, a growth hormone-releasing peptide, discloses protectant activity against cardiovascular damage in rats with isolated growth hormone deficiency. *Cardiologia*, 42:1165-1172; de Gennaro Colonna V., et al. (1997) Cardiac ischemia and impairment of vascular endothelium function in hearts from growth hormone-deficient rats: protection by hexarelin. *Eur J Pharmacol*, 334:201-207). Similar results are obtained in aged rats in which treatment with hexarelin resulted in a strong protection against the post ischemic ventricular dysfunction. Complete recovery of the cardiac function was observed in the reperfusion and the simultaneous reduction in the creatine kinase levels corroborated the integrity of the heart membranes and the preservation of the contractile weakness following the oxygen readmission. The hexarelin protective effect was also shown by the production of 6-keto-PGF 1a and the restoration of the coronary vascular reactivity to Angiotensin II (Rossoni G., de Gennaro Colonna V., et al. (1998) Protectant activity of hexarelin or growth hormone against post ischemic ventricular dysfunction in hearts from aged rats. *J Cardiovasc Pharmacol*, 32:260-265; Rossoni G., de Gennaro Colonna V., et al. (1998) Protectant activity of hexarelin or growth hormone against post ischemic ventricular dysfunction in hearts from aged rats. *J Cardiovasc Pharmacol*, 32:260-265; Locatelli V., Rossoni G., et al. (1999) Growth hormone-independent cardioprotective effects of hexarelin in the rat. *Endocrinology*, 140:4024-4031). Studies in hypophysectomised rats showed the GHS cardioprotective effects independents of GH and mediated by specific myocardial receptors (Locatelli V., Rossoni G., et. al. (1999) Growth hormone-independent cardioprotective effects of hexarelin in the rat. *Endocrinology*, 140:4024-4031; Bodart V., McNicoll N., et al. (1999) Identification and characterization of a new GHRP receptor in the heart. *Circ Res*, 85:796-808).

Hexarelin increases the systolic ejection volume and cardiac output, and reduces the total peripheral resistance in a 4 week rat model after the myocardial infarction induction. Although the mechanism of the synthetic GHS inotropic activity is not clear, there are evidence of the increase in the papillary muscle contractility by action on the endothelial cells or in the nerve endings (Tivesten A., Bollano et al. (2000). The growth hormone secretagogue Hexarelin improve cardiac function in rats after experimental myocardial infarction. *Endocrinology*, 141:60-66; Bedendi I., Gallo M. P., et al. (2001) Role of endothelial cells in modulation of contractility induced by hexarelin in rat ventricle. *Life Sci*, 69:2189-2201)

Ghrelin does not share all the cardiovascular actions of the synthetic GHS. Ghrelin gives a poor protection to the heart suggesting that the synthetic GHS effects are due to the binding and activation of GHS specific sites. Studies with [125I] Tyr-Ala-hexarelin revealed many binding sites in rat myocardium and in human cardiovascular tissues distinct of GHSR-1a, suggesting the existence of another receptor with a similar sequence to CD36 mediating the coronary actions of synthetic GHS (Torsello A., Bresciani E., et al. (2003) Ghrelin plays a minor role in the physiological control of cardiac function in the rat. *Endocrinology*, 144:1787-1792; Muccioli G., Broglio F., et al. (2000) Growth hormone-releasing peptides and the cardiovascular system. *Ann Endocrinol* (Paris) 61:27-31; Bodart V., Febbraio M., et al. (2002) CD36 mediates the cardiovascular action of growth hormone-releasing peptides in the heart. *Circ Res*, 90:844-849). Although ghrelin is mostly inactive at a coronary level, it does present other cardiovascular effects. Ghrelin has a very potent in vivo and in vitro vasodilating effect. Such ghrelin action is directed towards the non striated muscles with potency comparable to the natriuretic peptides. In human atherosclerosis patients ghrelin receptors are augmented suggesting that it plays a role on the compensation for the vasoconstriction increment observed in such condition. (Okumura H., Nagaya N., et al. (2002) Vasodilatory effect of ghrelin, an endogenous peptide from the stomach. *J Cardiovasc Pharmacol*, 39:779-783; Wiley K. E., Davenport A. P. (2002) Comparison of vasodilators in human internal mammary artery: ghrelin is a potent physiological antagonist of endothelin-1. Br. *J. Pharmacol*, 136:1146-1152; Katugampola S. D. (2001) [125I-His(9)]-ghrelin, a novel radioligand for localising GHS orphan receptors in human and rat tissue: up-regulation of receptors with atherosclerosis. Br J Pharmacol, 134:143-149).

Other studies showed that hexarelin, acylated ghrelin and even ghrelin can prevent doxorubicin induced cell death of H9c2 cardiomyocytes and endothelial cells, probably stimulating intracellular signalling like the activation of ERK1/2 and PI 3-kinase/AKT (Baldanzi G., Filigheddu N., et. al. (2002) Ghrelin and des-acyl ghrelin inhibit cell death in cardiomyocytes and endothelial cells through ERK1/2 and PI 3-kinase/AKT. *J Cell Biol*, 159:1029-1037; Filigheddu N., Fubini A., et al. (2001) Hexarelin protects H9c2 cardiomyocytes from doxorubicin-induced cell death. *Endocrine*, 14:113-119).

In vivo studies on cardiomyocytes and endothelial cells suggests that the antiapoptotic effects of GHS are mediated by the activation of ERK and AKT and by the inhibition of the activation of caspase 3 and BAX expression increasing the expression of BCL-2 (Pang J. J., Xu R. K., et al. (2004) Hexarelin protects rat cardiomyocytes from angiotensin II-induced apoptosis in vitro. *Am J Physiol Heart Circ Physiol*, 286:H1063-H1069). Such data enforces the hypothesis of the existence of another GHS-R subtype, because non acylated ghrelin does not activate GHS-R1a.

Ghrelin and GHS have cardiovascular activity in humans. Its administration to healthy volunteers and patients with chronic cardiac failure reduced the systemic vascular resistance and increase the cardiac output and the systolic ejection volume, with a reduction of the mean arterial pressure but not showing any change in the heart rate, pressure on the medial pulmonary artery or capillary pulmonary pressure. (Nagaya N., Kojima M., et al. (2001) Hemodynamic and hormonal effects of human ghrelin in healthy volunteers. *Am J Physiol Regul Integr Comp Physiol*, 280:R1483-R1487; Enomoto M., Nagaya N., et al. (2003) Cardiovascular and hormonal effects of subcutaneous administration of ghrelin, a novel growth hormone-releasing peptide, in healthy humans. *Clin Sci* (Loud), 105:431-435)

It has also been observed that several trophic factors, including GH and IGF-I have neuroprotecting properties during the second phase of in vivo hypoxic ischemia (HI) and has been shown that the activation of the PI3K pathway with AKT phosphorylation is the mediator of the neuronal survival rate in vitro induced by growth factors, phosphorylated AKT promoted cell survival and can inhibit apoptosis by inactivation of several antiapoptotic targets like Bad, glycogen synthase 3 beta (GSK3β), caspase 9 or transcriptional factor modification. (Kulik G., Klippel A., Weber M. J. (1997). Antiapoptotic signalling by the insulin-like growth factor I receptor, phosphatidylinositol 3-kinase, and Akt. *Mol Cell Biol*, 17:1595-1606)

Another pathway activated by growth factors is MAPK p42/44 ERK. ERK activation has been found to inhibit the hypoxia induced apoptosis. Besides the neuroprotection BDNF in neonatal rats has shown to be mediated by the activation of MAPK/ERK and treatment IGF-I after HI activates Akt and EKR (Buckley S., Driscoll B., et al. (1999) ERK activation protects against DNA damage and apoptosis in hyperoxic rat AEC2. *Am J Physiol*, 277:159-166; Han B. H., Holtzman D. M. (2000) BDNF protects the neonatal brain from hypoxic-ischemic injury in vivo via the ERK pathway. *J Neurosci*, 20:5775-5781).

Hexarelin reduces the brain damage on an in vivo model of HI. This protection is related to AKT and GSK3β phosphorylation indicating the possibility of the involvement of PI3K pathway. It's protective effect to cortex, hippocampus thalamus, but not in the striatum, spatial distribution of the protection is correlated to the localization of GH receptor and hexarelin (Brywe K. G., Leverin A.-L., et al. (2005) Growth Hormone Releasing Peptide Hexarelin reduces neonatal brain injury and alters Akt/Glycogen Synthase Kinase-3βphosphorylation. *Endocrinology*, 146: 4665-4672; Lobie P. E., Garcia-Aragon J., et al. (1993) Localization and ontogeny of growth hormone receptor gene expression in the central nervous system. *Dev Brain Res*, 74:225-233; Scheepens A., Sirimanne E. S., et al. (2001) Growth hormone as a neuronal rescue factor during recovery from CNS injury. *Neuroscience*, 104:677-687). Such findings suggest that the hexarelin protective effect could be GH mediated or GH and hexarelin share common pathways for the cell protection because GHS-R mRNA has been found in several of the brain structures. Administration of GHRP-6 to adult rats under physiological conditions showed an increase on the levels of IGF-I in hypothalamus, cerebellum, hippocampus but not in cortex. Although this could be due to the increase of the IGF-I expression, the same effect has not been found in hexarelin treated rats 24 hours after HI. On the other hand if IGF-I was an important mediator of hexarelin effects one could also expected expect a reduction of the brain damage in the striatum, since IGF-I receptors are present there. (Frago L. M., Paneda C., Dickson S. L., et al. (2002) Growth hormone (GH) and GH-releasing peptide-6 increase brain insulin-like growth factor-I expression and activate intracellular signalling pathways involved in neuroprotection. *Endocrinology*, 143:4113-4122; Guan J., Williams C., et al. (1993) The effects of IGF-I treatment after hypoxic-ischemic brain injury in adult rats. *J Cereb Blood Flow Metab*, 13:609-616). Hexarelin also activates PI3K pathway in the Central Nervous System (CNS) after HI but it does not affect ERK phosphorylation. IGF-I in contrast activates both ERK and PI3K pathways.

Hexarelin increases the phosphorylation of the IGF-I receptor. In the absence of an obvious induction of IGF-I, the phosphorylation increase could be due to a receptor transactivation by hexarelin or an endogenous ligand. Previously it has been reported that GPCR agonists like angiotensin-II, thrombin and endothelin can stimulate the IGF-I and/or AKT (Sumitomo M., Milowsky M. I., et al. (2001) Neutral endopeptidase inhibits neuropeptide-mediated transactivation of the insulin-like growth factor receptor-Akt cell survival pathway. *Cancer Res*, 61:3294-3298; Zahradka P., Litchie B., et al. (2004) Transactivation of the insulin-like growth factor-I receptor by angiotensin II mediates downstream signalling from the angiotensin II type 1 receptor to phosphatidylinositol 3-kinase. *Endocrinology*, 145:2978-2987).

The neuroprotective effect of hexarelin does not seem to be mediated primarily by an induction of the GH/IGF-I axis, although an increased signaling on the IGF-I receptor could contribute to the reduction of the brain damage.

DETAILED DESCRIPTION OF THE INVENTION

In spite of the vast work on this field, described in the state of the art, it is evident that all ghrelin mimetic compounds and those of non peptidic nature are not capable of exerting all possible functions attributed to ghrelin in the organism. Preferring the usage of compounds of peptidic nature, having a larger structural similarity, the description of such peptidic analogs is constrained however to the use of non natural D stereochemistry amino acids as part of the compositions.

Taking into account the importance of the peptidic secretagogues and the previously described functions and the capacity of such compounds on the endocrine and non endocrine functions in a large variety of organisms, systems and cells, the present invention describes, for the first time chemical molecules of a peptidic nature, with internal cycles and composed solely of amino acids with an L stereochemistry for the chiral carbon, capable of exerting due to their chemical structure, similar functions of those attributed to ghrelin, des-acyl ghrelin and other peptidic GHS, including but not restricted to the GH releasing capacity, cardioprotection and in general functional improving of the cardiac muscle and the reticuloendothelial system, neuroprotection that does not only includes the brain but all the nervous system cells, and the control and regulation of appetite including the regulation of fat and energy metabolism.

The peptidic chemical compounds described in the invention have a structure allowing them to fulfill the requirements to bind the ghrelin specific receptors and at the same time the receptors described for the binding of other secretagogues performing all of the aforementioned functions.

In a particular realization, the invention refers to chemical molecules having the following structure:

I.
$[Aa_1 \ldots Aa_n]X_1[Ab_1 \ldots Ab_n]X_2[Ac_1 \ldots Ac_n]$ $Ad_n$

Where Aa are L-amino acids selected from the set of [Cys, Gly, Ser, His, Ala, Leu, Met o Thr], varying in combinations of 1 to 4 residues, Ab are L-amino acids, selected from the set of [Pro, Ile, Ala, Phe, Trp, Lys, Asp, Asn, Glu, Gln, Gly, Leu, Met, Tyr o Thr], varying in combinations of 1 to 4 residues, Ac are L-amino acids selected from the set of [Arg, Leu, Pro, Val, Thr, Glu, His, Gln, Asn, Asp, Trp, Tyr, Phe, Ser, Ala, Gly o Ile], varying in combination of 1 to 5 and Ad are L-amino acids, natural or not without limit in number, $X_1$ y $X_2$ are L-amino acids, natural o not, with the side chains covalently bound forming an internal cycle, using any chemical reaction for the direct link or using a binding compound as a bridge.

Compounds belonging to the structural classes are shown as follows:

| A221 | GS<u>K</u>F<u>D</u>SPEHQ | (SEC. ID NO: 1) |
|---|---|---|
| A222 | HGS<u>K</u>F<u>D</u>LEFG | (SEC. ID NO: 2) |
| A223 | HC<u>K</u>F<u>D</u>LDWH | (SEC. ID NO: 3) |
| A224 | SS<u>D</u>F<u>K</u>LYWG | (SEC. ID NO: 4) |
| A225 | AL<u>D</u>F<u>K</u>PNIP | (SEC. ID NO: 5) |
| A226 | ST<u>D</u>F<u>K</u>PFAI | (SEC. ID NO: 6) |
| A227 | HS<u>K</u>GY<u>D</u>LDH | (SEC. ID NO: 7) |
| A228 | G<u>K</u>FG<u>D</u>LSPEHQ | (SEC. ID NO: 8) |
| A229 | HA<u>K</u>PGGI<u>D</u>PEQ | (SEC. ID NO: 9) |
| A230 | G<u>K</u>F<u>D</u>SPEHQ | (SEC. ID NO: 10) |
| A231 | GGG<u>K</u>FW<u>D</u>IPHH | (SEC. ID NO: 11) |
| A232 | H<u>K</u>GI<u>D</u>SPEQH | (SEC. ID NO: 12) |
| A233 | G<u>K</u>F<u>D</u>LSPEHQ | (SEC. ID NO: 13) |

-continued

| A234 | GD<u>A</u>GA<u>K</u>LLSSR | (SEC. ID NO: 14) |
| A235 | GM<u>E</u>AGI<u>K</u>LCHRQ | (SEC. ID NO: 15) |
| A236 | GE<u>G</u>Y<u>K</u>LDERSQ | (SEC. ID NO: 16) |
| A237 | GG<u>E</u>AG<u>K</u>LCPPRY | (SEC. ID NO: 17) |
| A238 | GL<u>E</u>F<u>K</u>LLHQ | (SEC. ID NO: 18) |

Where the underlined amino acids are linked by the side chains.

The aforementioned molecules were described for the function by the exhaustive molecular modelling of the human ghrelin receptor using combined techniques of homology modelling, molecular dynamics and exhaustive conformational search techniques.

Once the receptor was modeled, binding models were built based in the modelling of ghrelin and other secretagogues. Based upon the receptor-ligand interactions, a virtual library was built with several thousand structures having such characteristics to perform a conformational analysis, and a massive docking experiment was performed against the receptor model.

Based on this analysis a series of compounds were selected representing several structural families that were chemically synthesized and tested with several in vivo and in vitro systems, after the biological assays the compounds were reoptimized and new libraries were generated and the structural analysis was repeated to seek for a larger action on the biological systems, having more specific structural regularities.

The invention also includes any homolog variant of the aforementioned compounds. Being understood as "homolog variant" any molecule of chemical nature similar in 70% or more of the amino acid sequence to those described in this invention, including non-natural amino acids, with a structure allowing it to perform the same effect of the hereby described compounds.

In another preferred realization of the invention, the pharmaceutical composition contains one or more of the described compounds or its allowed salts, along with acceptable additive or vehicles for the application purpose. Also it is part of the present invention, the use of the compounds for the manufacturing of medicines, nutritional supplements, or other formulations of human or animal use in aquaculture or other breeding or animal improvement activities, in vivo, in vitro, in body associated devices or in devices for controlled release to the medium, associated to the action similar to other GHS, directly related or not to their endocrine action.

The molecules described herein were defined by the capacity of interacting to the human ghrelin receptor, but we can not rule out another proteins not having similar structure or amino acid sequence but have the capacity to bind this type of compound and affect in any way their biological action being by activation, potentiation, repression, competition or synergism with other substrates, or by any mechanism, described or not but experimentally documented.

For the definition of the chemical compounds described in the invention, the molecular modelling of the human ghrelin receptor was performed, using combined techniques of homology modelling, molecular dynamics and exhaustive conformational search techniques. Once the receptor was modelled binding models were built based in the modelling of ghrelin and other secretagogues. Based upon the receptor-ligand interactions a virtual library was built with several thousand structures having such characteristics to perform a conformational analysis, and a massive docking experiment was performed against the receptor model.

Based on this analysis a series of compounds were selected representing several structural families that were chemically synthesized and tested with several in vivo and in vitro systems, after the biological assays the compounds were reoptimized and new libraries were generated and the structural analysis was repeated with another round of molecular docking with the receptor to extract structural regularities, the chemical nature of the second round was optimized to reach higher values of calculated binding energy, ranging between −58 and −32 KJ/mol and analyzed again to look for a larger action on the biological systems, having more specific structural regularities. A representative selection of 18 such compounds with binding energies better than −40 KJ/mol, were synthesized, purified using High Performance Liquid Chromatography, analyzed by Mass Spectrometry and evaluated for the in vivo and in vitro effectiveness.

EXAMPLES

Figure 1A:
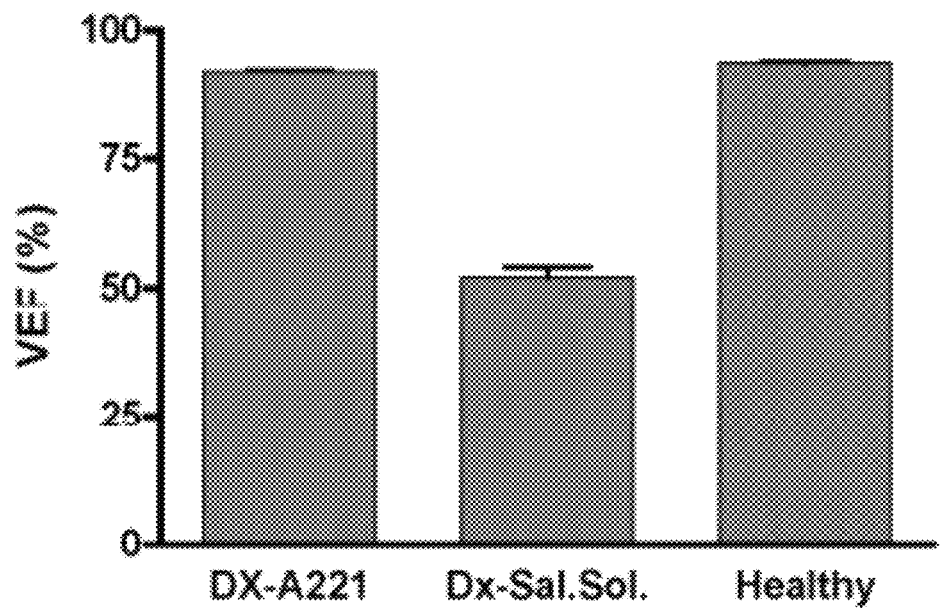
FIG. 1: Effects of the treatment with compounds A221 (a), A228(b) y A233(c) in the prevention of Doxorubicin (Dx) induced myocardial failure.

The present invention is explained in the following examples:

Example 1

Selection of the Compounds by in Silico Molecular Modelling

The compounds obtained in the second cycle of the computational evaluation as described above were optimized to obtain better energy values and more specific regularities upon receptor binding, 18 representative compounds with energies better than −40 KJ/mol were selected as shown in table 1.

TABLE 1

Calculated interaction energy of the interaction with the Growth Hormone Secretagogue Receptor model after molecular docking.

| Compound | Energy (KJ/mol) |
| --- | --- |
| A221 | −52.54 |
| A222 | −49.80 |
| A223 | −43.76 |
| A224 | −42.93 |
| A225 | −54.99 |
| A226 | −40.00 |
| A227 | −41.01 |
| A228 | −40.93 |
| A229 | −52.25 |
| A230 | −56.27 |
| A231 | −42.32 |

TABLE 1-continued

Calculated interaction energy of the interaction with the Growth Hormone Secretagogue Receptor model after molecular docking.

| Compound | Energy (KJ/mol) |
|---|---|
| A232 | −50.30 |
| A233 | −58.06 |
| A234 | −53.14 |
| A235 | −45.94 |
| A236 | −45.20 |
| A237 | −50.01 |
| A238 | −51.11 |

Example 2

Prevention of NGF Deprivation Induced Death on PC12 Cells

PC12 cells were stored in 75 cm$^2$ culture flasks on DMEM containing 5% bovine foetal serum and 10% horse serum, with 50 μg/ml gentamicin. Cells were incubated at 37° C. in 5% $CO_2$. To induce differentiation cells were transferred at a density of 1×10$^4$ to polylysine covered 96 well plates in NGF supplemented DMEM media for 7 days, with medium replacement every 2-3 days. After differentiation cells were incubated with peptidic GHS analog compounds, at different concentrations for 72 h. Cell survival and proliferation was determined using the Promega non-radioactive cytotoxicity proliferation assay, Cell Titer 96, based in the conversion of 3-(4,5-dimethylthiazole-2-yl)-2,5-diphenyltetrazolium bromide (MTT) in to a spectrophotometrically detectable product. After deprivation of NGF medium is removed and 15 μl of the DMEM dissolved dye is added, after 4 hours of 37° C. incubation 100 μl of the stopping solution is added and absorbance is measured at 570 nm The compounds showed a concentration dependent neuroprotection effect, IC50 for each of the compounds is shown in Table 2.

TABLE 2

IC50 values of each compound during the NGF deprivation induced neuronal death.

| Compound | IC50 uM |
|---|---|
| A221 | 2.02 |
| A222 | 2.03 |
| A223 | 3.12 |
| A224 | 2.37 |
| A225 | 4.07 |
| A226 | 4.87 |
| A227 | 3.06 |
| A228 | 3.99 |
| A229 | 3.41 |
| A230 | 4.06 |
| A231 | 4.00 |
| A232 | 4.89 |
| A233 | 5.00 |
| A234 | 5.86 |
| A235 | 2.05 |
| A236 | 3.00 |
| A237 | 3.33 |
| A238 | 2.04 |

Example 3

Prevention of the Induced Neuronal Damage by Hydrogen Peroxide Addition to a Primary Culture of Neurons Primary cultures of granular cerebellum cells were obtained from 7-9 days Wistar rats. After a rapid dissection, rat cerebellums were submerged in a cold solution and meningeal membranes were removed, each organ was transferred to a 2-3 ml fresh medium solution and finely sliced. Cells were dissociated using a Pasteur pipette and filtered through a nylon 40 mu.M membrane (Falcon, Franklin Lakes, N.J.). The number of viable cells was determined by cell counting in a hematocytometer with tripan blue as a marker. Cells were cultured on polylysine covered 96 well plates at a density of 6250 cells in 200 ml final volume. Cultures were kept at 37° C. in 5%. $CO_2$ after 24 h, 10 μM of cytosine arabinofuranose (AraC; Sigma) was added to inhibit the proliferation of non-neuronal cells.

The capacity of neural damage prevention was tested adding 500 μM hydrogen peroxide in different concentrations of peptidic GHS analog compounds, Cell survival was determined using the Promega non-radioactive cytotoxicity proliferation assay, Cell Titer 96 (Promega).

The compounds showed a concentration dependent neuroprotection effect, IC50 for each of the compounds is shown in Table 3.

TABLE 3

IC50 values of each compound during the induced neuronal damage by Hydrogen Peroxide addition to a primary culture of neurons.

| Compound | IC50 uM |
|---|---|
| A221 | 1.80 |
| A222 | 1.30 |
| A223 | 2.47 |
| A224 | 3.20 |
| A225 | 3.99 |
| A226 | 3.58 |
| A227 | 2.26 |
| A228 | 1.77 |
| A229 | 1.33 |
| A230 | 3.81 |
| A231 | 3.46 |
| A232 | 3.28 |
| A233 | 3.56 |
| A234 | 3.72 |
| A235 | 1.01 |
| A236 | 3.33 |
| A237 | 2.51 |
| A238 | 1.00 |

Example 4

Demonstration of the Biological Activity of the Peptidic GHS Analog Compounds in Fish IGF-I mRNa was determined in the liver of intraperitoneally injected tilapias monitoring also the GH level time course, showing the peptidic GHS analog compounds as able to stimulate in fish the GH levels in the bloodstream and at incrementing the IGF-I mRNA levels after the injection of the compounds as shown in table 4.

TABLE 4

Normalized IGF-I mRNA levels to a non related synthetic peptide control group.

| Compound | IGF1 |
|---|---|
| A221 | 1.32 |
| A222 | 1.115 |
| A223 | 1.40 |
| A224 | 1.41 |
| A225 | 1.38 |
| A226 | 1.13 |
| A227 | 1.28 |
| A228 | 1.18 |
| A229 | 1.09 |
| A230 | 1.48 |
| A231 | 1.39 |
| A232 | 1.23 |
| A233 | 1.69 |
| A234 | 1.17 |
| A235 | 0.9 |
| A236 | 1.13 |
| A237 | 1.201 |
| A238 | 1.24 |

Example 5

Experiment on Juvenile Tilapia Treated with Peptidic GHS Analog Compounds 5.1 Growth Acceleration on Tilapias Treated Intraperitoneally (ip) with Peptidic GHS analog compounds.

The compounds were dissolved in a sodium phosphate (PBS) buffer solution and injected twice a week, during three weeks at 0.1 µg/g of humid fish weight (gbw). Compounds were applied individually to a group of 10 male tilapias with an average weight of 60.41±10.36 g and a control group with an average weight of 60.58±19.67 g was receiving PBS only as a control, measuring the average weight every week, all animals in the experiment were labelled with microchips (Stoelting Co. Wood Dale, USA.). for proper identification. A weight increase was obtained in the treated group with 165% peak relative to the control group as shown in table 5.

TABLE 5

Weight increment in % for the treated group taking as 100% the growing of the control group.

| Compound | Weight Inc. (%) |
|---|---|
| A221 | 98.0 |
| A222 | 96.2 |
| A223 | 105.0 |
| A224 | 132.7 |
| A225 | 120.0 |
| A226 | 122.4 |
| A227 | 139.9 |
| A228 | 130.6 |
| A229 | 126.5 |
| A230 | 158.0 |
| A231 | 150.2 |
| A232 | 160.1 |
| A233 | 165.0 |
| A234 | 110.6 |
| A235 | 89.9 |
| A236 | 99.0 |
| A237 | 100.0 |
| A238 | 129.4 |

In the same experiment we have studied the presence of monogeneous Trichodinics and Helmints on the animals used in the assay to observe and compare the extension of the invasion of pathogenic agents in the treated group. Table 6 shows the comparison with the non treated animals that showed six crosses as average.

TABLE 6

Intensity of the pathogenic infection with Trichodinics and Helmints in treated animals.

| Compound | Pathogens |
|---|---|
| A221 | +++++ |
| A222 | ++++ |
| A223 | ++++ |
| A224 | ++++ |
| A225 | ++++ |
| A226 | +++ |
| A227 | ++++ |
| A228 | +++ |
| A229 | +++ |
| A230 | ++ |
| A231 | ++ |
| A232 | ++ |
| A233 | ++ |
| A234 | +++ |
| A235 | +++ |
| A236 | ++++ |
| A237 | +++ |
| A238 | +++ |

5.2 Stimulation by Immersion, of the Growth of Tilapia (*Oreochromis* Sp) Larvae with the Peptidic GHS Analogs.

Growth stimulation experiments on tilapia *Oreochromis* sp. larvae were performed evaluating groups of 100 larvae with 0.01 g average, using the peptidic GHS analogs, in a 100 µg/L concentration, twice a week using an immersion time of one hour. On a three weeks course a top growth stimulation of 155% of average weight was obtained as shown in table 7, relative to the control group that was receiving PBS immersions.

TABLE 7

Weight increment in % for the treated group taking as 100% the growing of the control group.

| Compound | Weight Inc. (%) |
|---|---|
| A221 | 97.0 |
| A222 | 96.0 |
| A223 | 102.0 |
| A224 | 130.0 |
| A225 | 98.0 |
| A226 | 120.4 |
| A227 | 140.6 |
| A228 | 132.0 |
| A229 | 125.0 |
| A230 | 150.0 |
| A231 | 151.0 |
| A232 | 148.3 |
| A233 | 155.0 |
| A234 | 120.6 |
| A235 | 90.0 |
| A236 | 105.0 |
| A237 | 109.9 |
| A238 | 112.6 |

During this experiment lysozyme levels were also monitored and an increase of this immunity marker was obtained in the treated animals as shown in table 8.

TABLE 8

Lysozyme levels of the treated animals relative to the control group.

| Compound | Lysozyme |
|---|---|
| A221 | 1.01 |
| A222 | 1.43 |
| A223 | 1.52 |
| A224 | 1.37 |
| A225 | 1.43 |
| A226 | 1.17 |
| A227 | 1.52 |
| A228 | 1.08 |
| A229 | 1.15 |
| A230 | 1.33 |
| A231 | 1.89 |
| A232 | 2.41 |
| A233 | 2.68 |
| A234 | 2.77 |
| A235 | 1.90 |
| A236 | 1.42 |
| A237 | 1.01 |
| A238 | 1.33 |

Example 6

Growing of Shrimps v *Litopenaeus Vanamei* by Dipping in a Solution of the Peptidic GHS Analogs Shrimp larvae were subjected two four dips, for one hour every three days with different peptidic GHS analogs at 0.1 g/L. The control group was subjected to the same frequency of dipping with 1 mg/L BSA.

As a result it was observed that in the treated group the quality of the larvae was improved with a 120-150% weight gain and 10-25% of size increase as shown in table 9, showing also a larger number of gill ramifications and rostral modifications. Besides it was found that n general in the treated group the animals had a lower muscular water content and better values of RNA/DNA, Protein/DNA, showing the higher activation of the metabolism in the treated larvae.

TABLE 9

Weight and size increment in % for the treated group taking as 100% the growing of the control group.

| Compound | Weight Inc. (%)/Size Inc. (%) |
|---|---|
| A221 | 120.1/112.0 |
| A222 | 121.0/112.2 |
| A223 | 120.0/110.9 |
| A224 | 127.0/116.0 |
| A225 | 121.0/112.6 |
| A226 | 120.1/112.2 |
| A227 | 128.6/118.5 |
| A228 | 128.2/118.9 |
| A229 | 126.1/115.9 |
| A230 | 150.0/123.6 |
| A231 | 130.0/123.0 |
| A232 | 132.8/123.0 |
| A233 | 143.0/124.9 |
| A234 | 123.6/114.2 |
| A235 | 121.0/112.5 |
| A236 | 121.0/112.0 |
| A237 | 127.0/116.2 |
| A238 | 129.2/117.9 |

This experiment was also performed in production conditions for compounds A221, A228 y A233, with a 20% of higher survival compared with the controls, keeping a stimulation of 110% on the weight and 30% in the size, showing on the treated animals a better homogeneity on the size distribution with only a 30% and a 8% of variation coefficient in weight and size respectively, on contras with a 77% and 30% in the non treated group.

Example 7

Growth Stimulation in Shrimps by the Dietary Supplementation with the Peptidic GHS Analogs The peptidic GHS analogs were included at 1% in a post-larvae crustacean diet. Post-larvae of *Litopenaeus vanamei* were fed with the aforementioned diet in parallel with a control group with 1% BSA addition. The effect was measured with an optical micrometer and weighing the animals in a 0.1 mg precision scale.

The added compound produced a size increase of 30-40% compared with the control group as shown in table 10.

TABLE 10

Size increment in % for the treated group taking as 100% the growing of the control group.

| Compound | Size Inc. (%) |
|---|---|
| A221 | 130.0 |
| A222 | 131.0 |
| A223 | 131.6 |
| A224 | 131.2 |
| A225 | 130.0 |
| A226 | 130.4 |
| A227 | 139.0 |
| A228 | 140.0 |
| A229 | 140.0 |
| A230 | 140.0 |
| A231 | 140.1 |
| A232 | 139.7 |
| A233 | 140.1 |
| A234 | 138.6 |
| A235 | 137.0 |
| A236 | 137.0 |
| A237 | 132.0 |
| A238 | 130.1 |

7.1: Artemia Salina Encapsulation

The peptidic GHS analogs were bioencapsulated in Artemia to be fed to *Litopenaeus vanamei* post-larvae. For the encapsulation the compounds were added in a 10 mh/L left for an hour, harvested and washed. The animals were fed four times a day for one month while the control group was fed with BSA encapsulated Artemia The effect was measured with an optical micrometer and weighing the animals in a 0.1 mg precision scale. The encapsulated compounds increased the growth of the animals in a 30 to 40% respect to the control group with a highly significant difference ($p<0.001$) as shown in table 11.

TABLE 11

Size increment in % for the treated group taking as 100% the growing of the control group.

| Compound | Size Inc. (%) |
|---|---|
| A221 | 130.2 |
| A222 | 130.3 |
| A223 | 132.0 |
| A224 | 130.0 |
| A225 | 130.0 |
| A226 | 132.0 |
| A227 | 140.0 |
| A228 | 140.0 |

TABLE 11-continued

Size increment in % for the treated group taking
as 100% the growing of the control group.

| Compound | Size Inc. (%) |
|---|---|
| A229 | 140.0 |
| A230 | 140.0 |
| A231 | 140.2 |
| A232 | 139.6 |
| A233 | 140.0 |
| A234 | 135.0 |
| A235 | 134.2 |
| A236 | 138.0 |
| A237 | 136.0 |
| A238 | 140.0 |

Example 8

Cardioprotective Effect in Rats of the Peptidic GHS Analogs

Figure 1B:
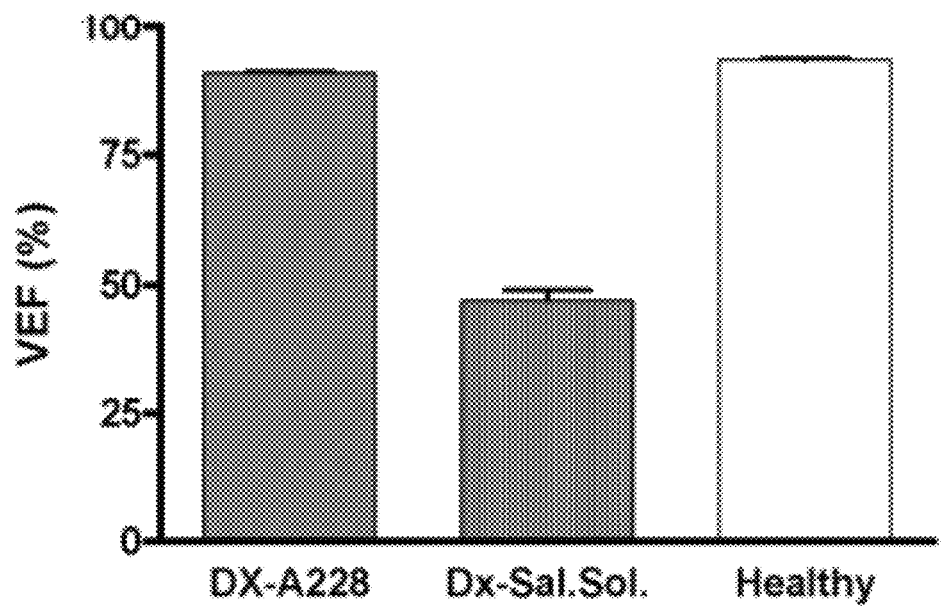
Figure 1C:
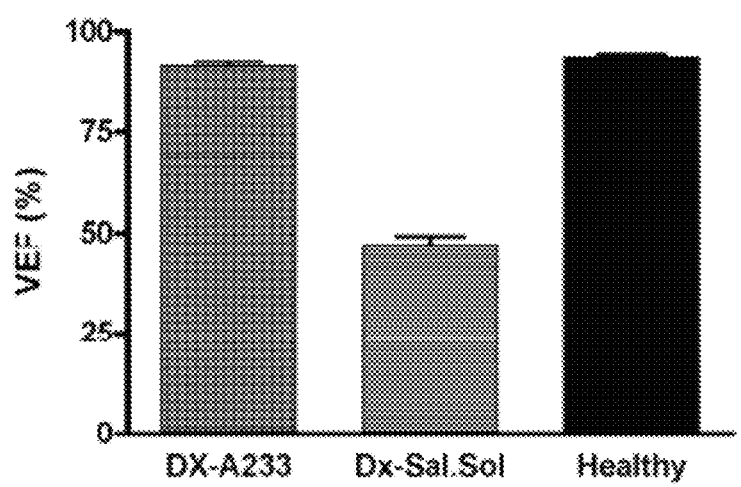
Figure 2A:
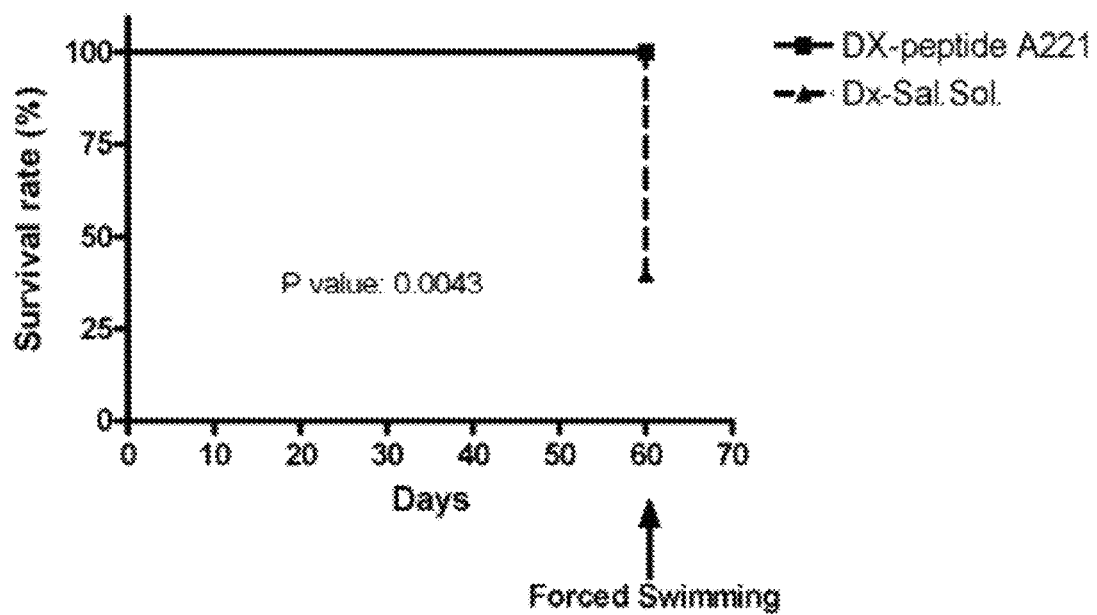
FIG. 2: Protective effect of compounds A221(a), A228(b) y A233(c) on forced stress in Dx treated rats.
Figure 2B:
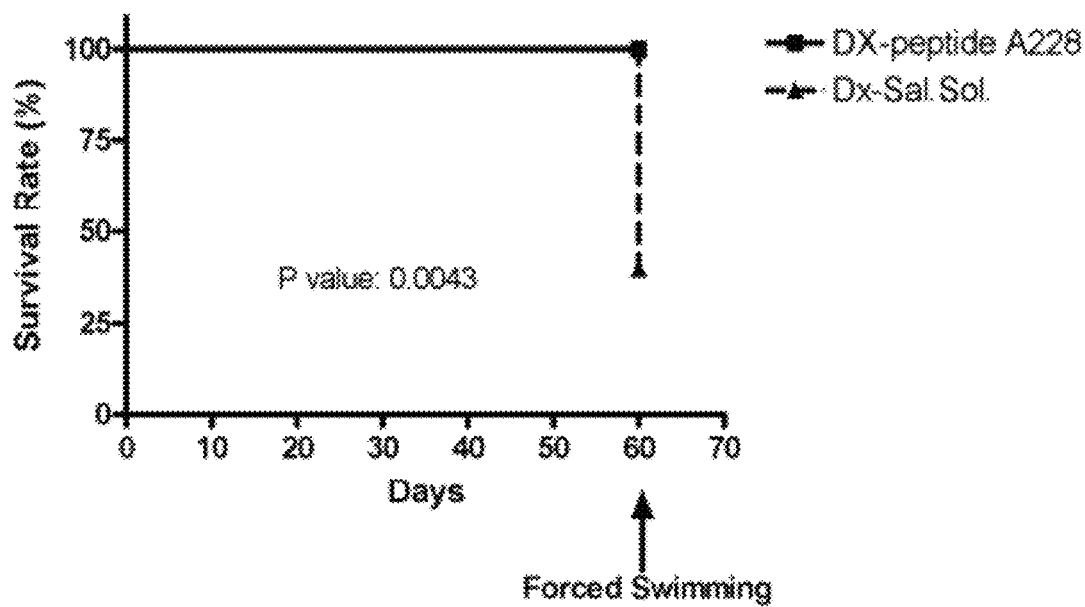
Figure 2C:
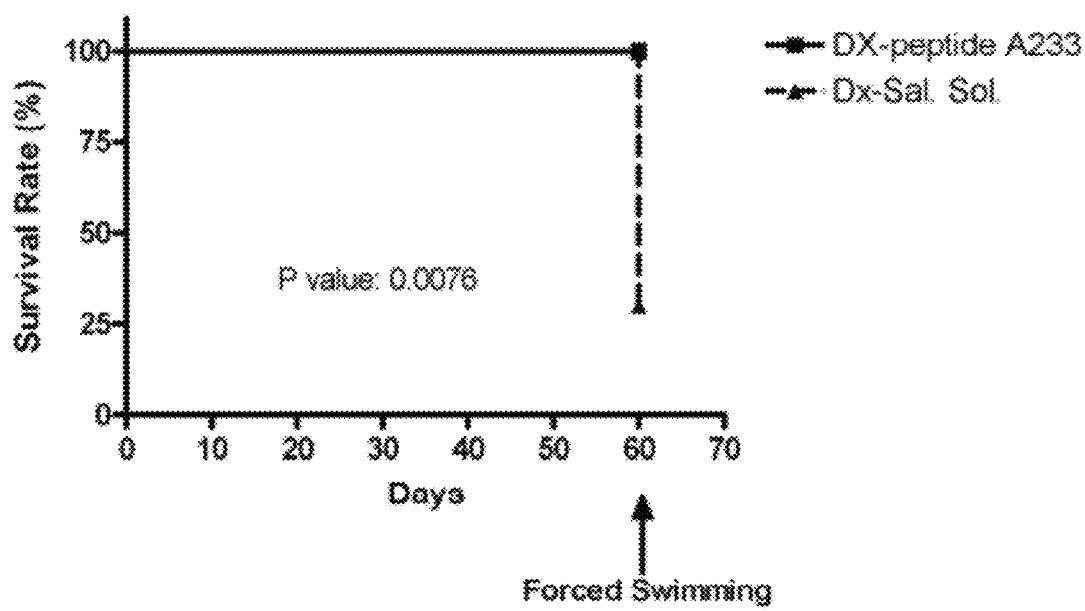
Figure 3A:
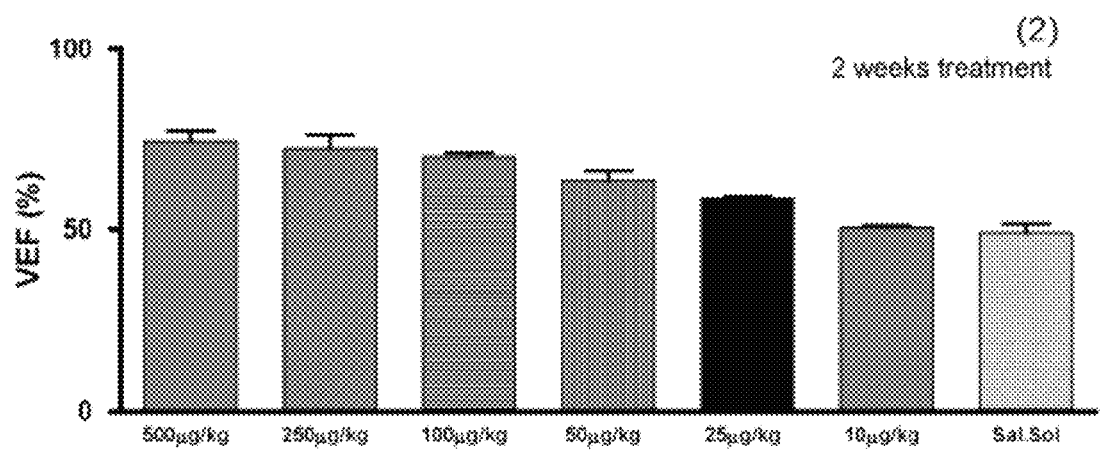
FIG. 3: Effect of the treatment with compounds A221 (a), A228(b) y A233(c) in time and reversion of Doxorubicin induced dilated cardiomyopathy in treated groups with doses ranging from 100 to 500 µg/kg of animal weight.
Figure 3A:
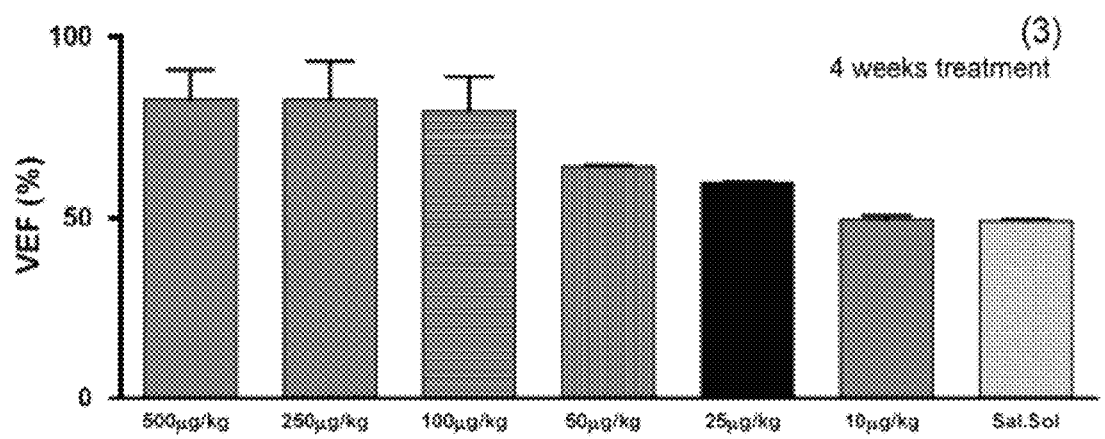
Figure 3B:
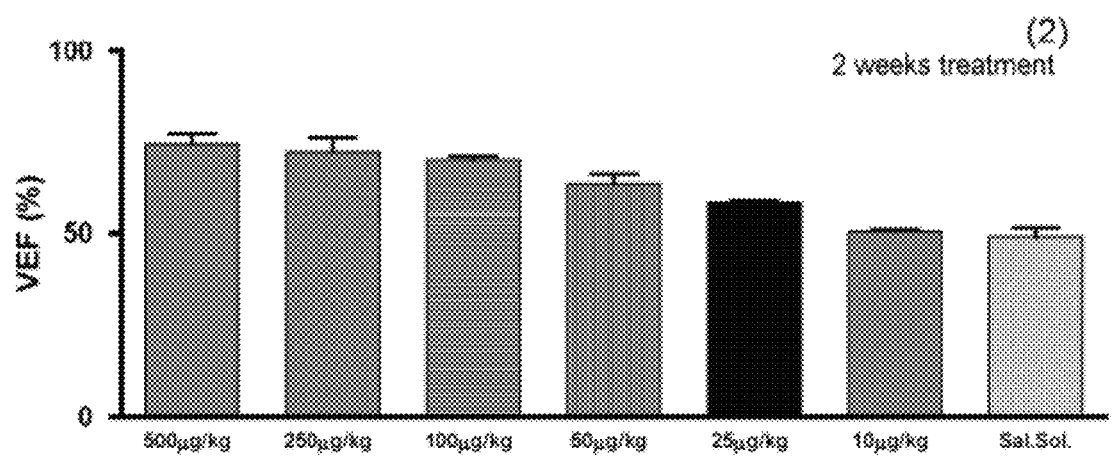
Figure 3B:
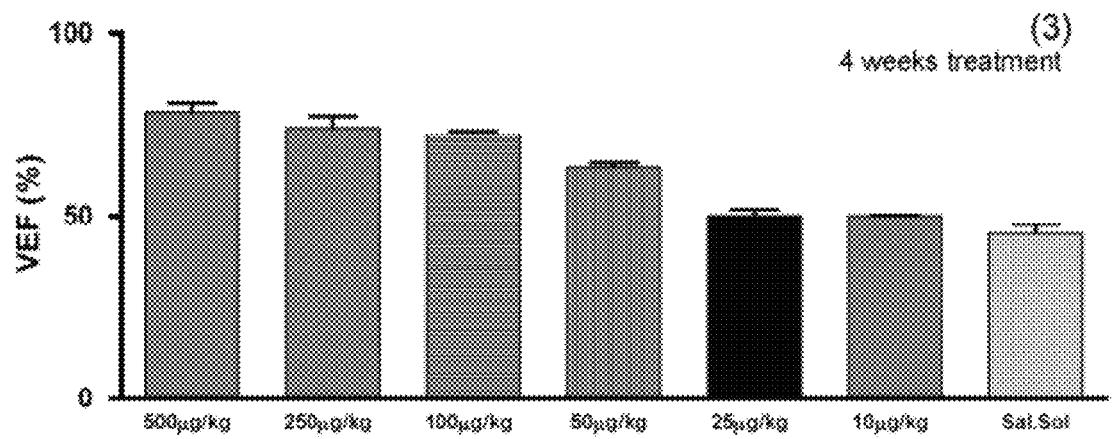
Figure 3C:
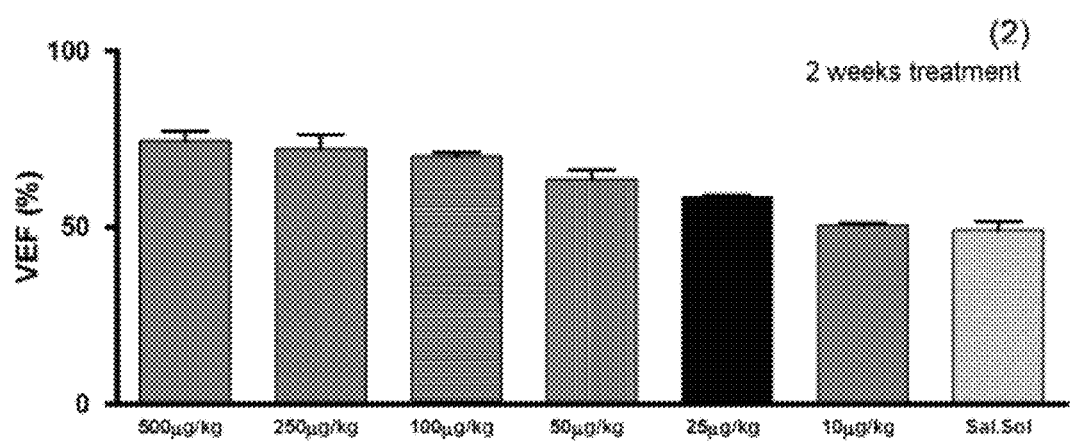
Figure 3C:
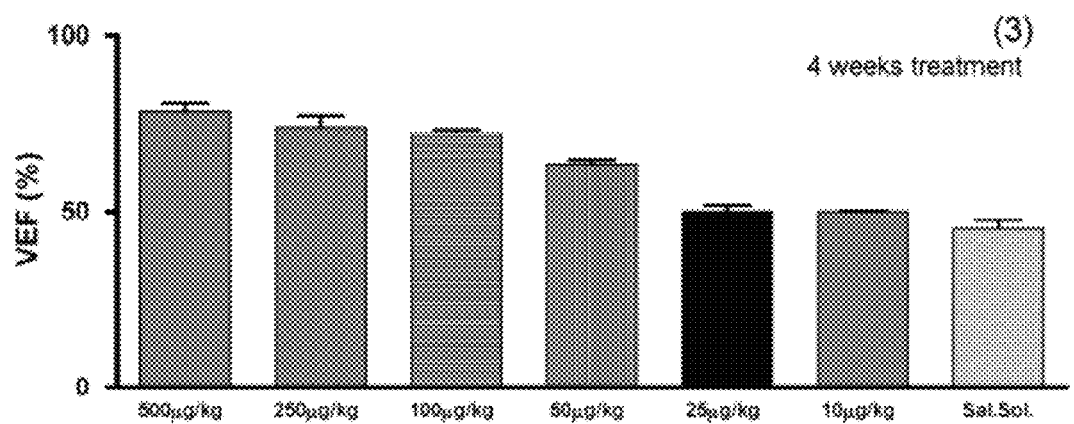

To reproduce the physiopathogenic effects of a Dilated Cardiomyopathy (DCM) female Wistar rats of 160 g were treated with 2 mg/kg Doxorubicin (Dx) during 8 weeks. A group of this rats was also treated in parallel with compounds A221, A228 or A233 intraperitoneally at 500 μg/Kg during the 8 weeks of Dx treatment, another Dx treated group was also receiving saline solution as a placebo, and as a healthy control for the experiment another group of untreated Wistar rats of the same age was used. After the 8 week treatment all the rats were tested with an echocardiogram, to test the ventricular functionality and assess the ventricular ejection fraction (VEF). As seen in FIG. 1 rats receiving the parallel Dx-compound A221(1a), A228(1b) or A233(1c) slightly modified VEF (p>0.05) with respect to the healthy control, in contrast the group receiving placebo suffers a drop in VEF of about a 40% (p<0.01), relative to the healthy control group. To demonstrate the functional implications for the stress response of the drop in VEF, the rats were subjected to forced swimming in 4° C. water foe 30 minutes, as shown in FIG. 2 animals receiving the treatment with Dx-compound A221 (2a), A228(2b) or A233(2c) have a survival of 100% and the Dx-saline solution survived to the 45% (p=0.0043). This results suggested that the protection by compounds A221, A228 ad A233, does not only maintains the VEF but also yields the heart resistant to forced stress.

Example 9

Cardioprotective Effect and Reversion of the Dilated Cardiomyopathy (DCM) in Rats of the Peptidic GHS Analogs To assess if there is any dose-response effect and reversion of DCM, Wistar rats were subjected to a treatment with 2 mg/kg of Doxorubicin (Dx) for 8 weeks, after the treatment all rats with a VEF drop higher than 40% were selected, divided in groups of n=8 and treated with different doses of compounds A221, A228 or A233 as follows:
500 μg/kg,
250 μg/kg,
100 μg/kg,
50 μg/kg,
25 μg/kg,
10 μg/kg
Saline Solution.
Defining the groups based in the A221 doses.

Figure 4A:
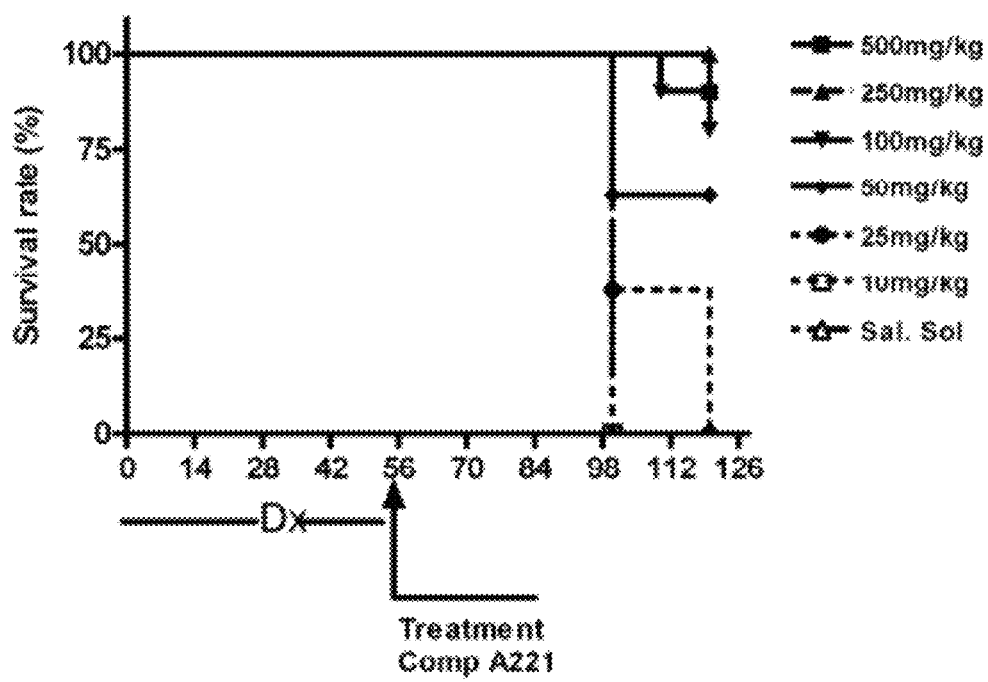
FIG. 4: Effect of the treatment with compounds A221 (a), A228(b) y A233(c) in the survival of animals with doxorubicin (Dx) induced dilated cardiomyopathy.
Figure 4B:
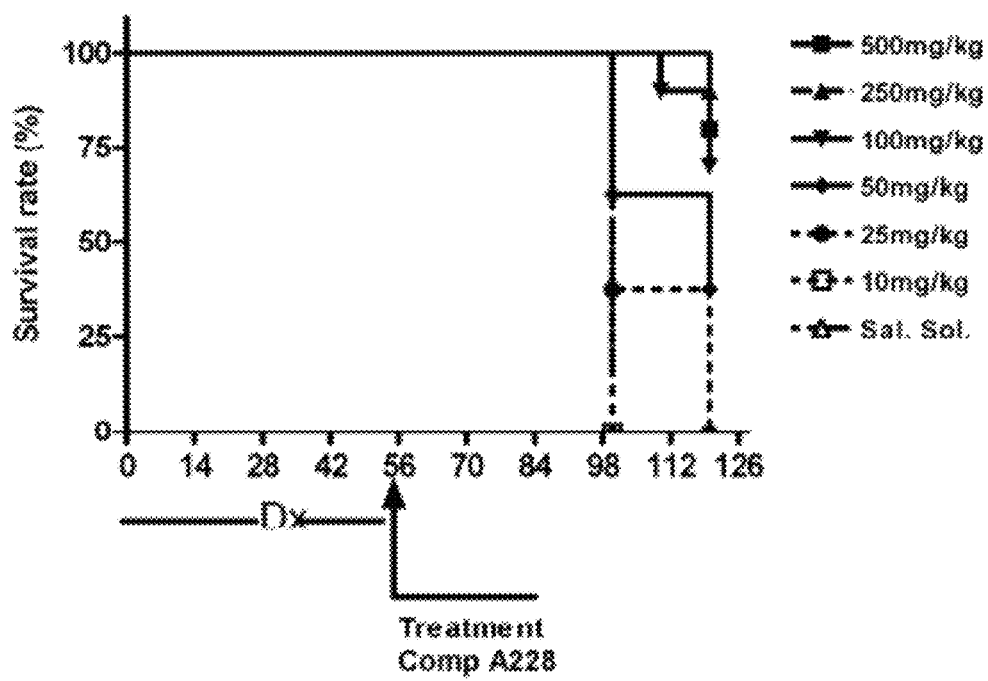
Figure 4C:
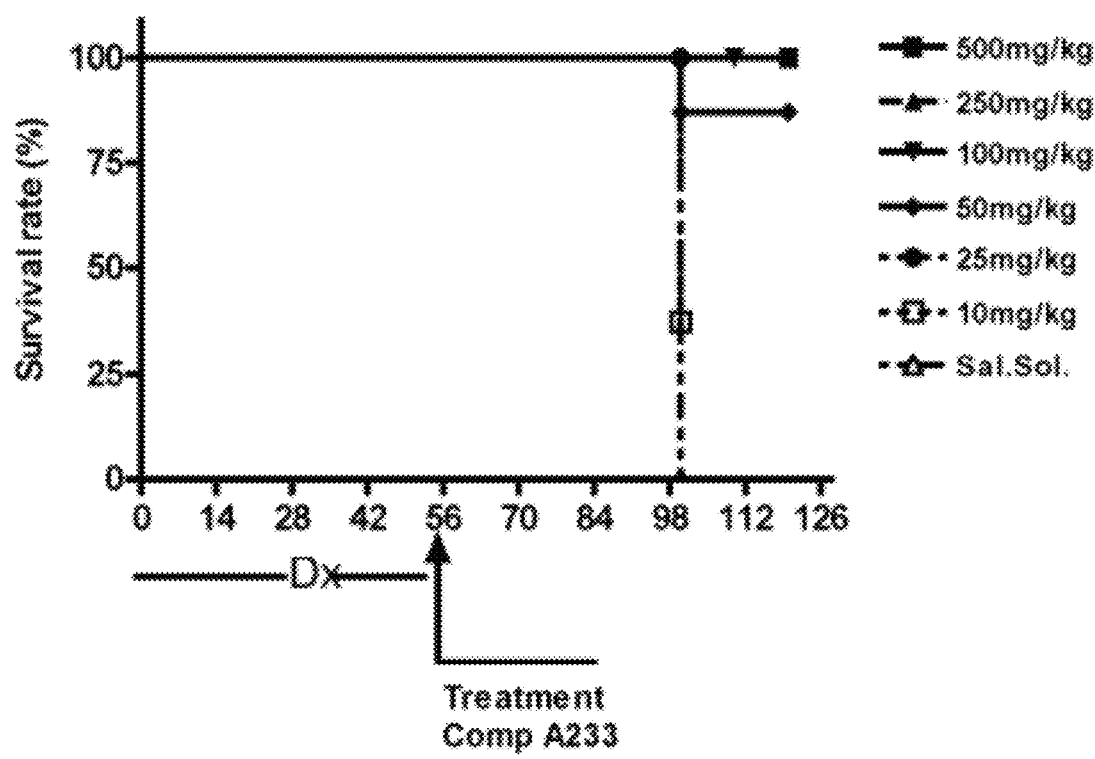

As shown in FIG. 3, two weeks after the treatment with compounds A221(3a), A228(3b) or A233(3c) partially reverts DCM in the concentration range of 50 μg/kg to 500 μg/kg but at 4 weeks of treatment the DCM reversion is complete in the groups receiving the compounds A221, A228 or A233 in the 100 to 500 μg/kg range, 50 μg/kg dosage is not effective for the total VEF recovery but somehow effective to reduce mortality in the group, respect to the animals receiving placebo or groups treated with lower concentrations, that do not recovered VEF and have a lower survival days after the treatment is finished. (FIG. 4, a A221, b A228 and c A233).

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Aug. 28, 2008. The sequence listing.txt file is 5 kb in size.

The invention claimed is:

1. A peptide having an amino acid sequence selected from the group consisting of SEQ ID NOS: 1-18.

2. A pharmaceutical composition comprising one or more of the peptides described in claim 1, or pharmaceutically acceptable salts thereof, and an excipient or vehicle.

3. A pharmaceutical composition according to claim 2, wherein said peptides are present in a range from 2 to 100 μg per ml in said composition.

4. A veterinary composition comprising one or more of the peptides described in claim 1, or veterinary acceptable salts thereof, and an excipient or vehicle.

* * * * *

UNITED STATES PATENT AND TRADEMARK OFFICE
CERTIFICATE OF CORRECTION

PATENT NO. : 8,367,620 B2
APPLICATION NO. : 12/281085
DATED : February 5, 2013
INVENTOR(S) : Rodriguez Fernandez et al.

It is certified that error appears in the above-identified patent and that said Letters Patent is hereby corrected as shown below:

In the Specifications:

Column 2, line 15

Now reads: "Patchett A.A.,

Nargund R.P., et al.";

Should read: -- Patchett A.A., Nargund R.P., et al. --.

Column 2, line 44

Now reads: "suggesting that is secreted";

Should read: -- suggesting that it is secreted --.

Column 2, line 60

Now reads: "has being described as";

Should read: -- has been described as --.

Column 8, line 23

Now reads: "could be mediates by the";

Should read: -- could be mediated by the --.

Column 10, line 55

Now reads: "and reperfusion Such protective";

Should read: -- and reperfusion. Such protective --.

Signed and Sealed this
Twenty-first Day of May, 2013

Teresa Stanek Rea
*Acting Director of the United States Patent and Trademark Office*

Column 11, line 48

Now reads:     "CD36mediating the coronary";

Should read:     -- CD36 mediating the coronary --.

Column 13, line 25

Now reads:     "also expected expect a reduction of the";

Should read:     -- also expect a reduction of the --.

Column 21, line 28

Now reads:     "were subjected two four dips";

Should read:     -- were subjected to four dips --.

Column 21, line 37

Now reads:     "found that n general";

Should read:     -- found that in general --.

Column 22, line 3

Now reads:     "on contras with a 77%";

Should read:     -- in contrast with a 77% --.

Column 22, line 48

Now reads:     "Artemia The effect";

Should read:     -- artemia. The effect --.

Column 23, line 40

Now reads:     "water foe 30 minutes";

Should read:     -- water for 30 minutes --.

Column 24, line 2

Now reads:     "A228 ad A233, does not only maintains";

Should read:     -- A228 and A233, not only maintains --.

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial sequence
<220> FEATURE:
<223> OTHER INFORMATION: Synthetic peptide with cycle on the side chains
      of Lys3 and Asp5.

<400> SEQUENCE: 1

Gly Ser Lys Phe Asp Ser Pro Glu His Gln
 1               5                  10

<210> SEQ ID NO 2
<211> LENGTH: 10
<212> TYPE: PRT
<213> ORGANISM: Artificial sequence
<220> FEATURE:
<223> OTHER INFORMATION: Synthetic peptide with cycle on the side chains
```

```
              of Lys4 and Asp6.

<400> SEQUENCE: 2

His Gly Ser Lys Phe Asp Leu Glu Phe Gly
 1               5                  10

<210> SEQ ID NO 3
<211> LENGTH: 9
<212> TYPE: PRT
<213> ORGANISM: Artificial sequence
<220> FEATURE:
<223> OTHER INFORMATION: Synthetic peptide with cycle on the side chains
      of Lys3 and Asp5.

<400> SEQUENCE: 3

His Cys Lys Phe Asp Leu Asp Trp His
 1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide with cycle on the side chains
      of Asp3 and Lys5.

<400> SEQUENCE: 4

Ser Ser Asp Phe Lys Leu Tyr Trp Gly
 1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide with cycle on the side chains
      of Asp3 and Lys5.

<400> SEQUENCE: 5

Ala Leu Asp Phe Lys Pro Asn Ile Pro
 1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide with cycle on the side chains
      of Asp3 and Lys5.

<400> SEQUENCE: 6

Ala Leu Asp Phe Lys Pro Asn Ile Pro
 1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide with cycle on the side chains
      of Lys3 and Asp6.

<400> SEQUENCE: 7

His Ser Lys Gly Tyr Asp Leu Asp His
 1               5

<210> SEQ ID NO 8
<211> LENGTH: 11
```

```
<212> TYPE: PRT
<213> ORGANISM: Artificial sequence
<220> FEATURE:
<223> OTHER INFORMATION: Synthetic peptide with cycle on the side chains
      of de Lys2 and Asp5.

<400> SEQUENCE: 8

Gly Lys Phe Gly Asp Leu Ser Pro Glu His Gln
 1               5                  10

<210> SEQ ID NO 9
<211> LENGTH: 11
<212> TYPE: PRT
<213> ORGANISM: Artificial sequence
<220> FEATURE:
<223> OTHER INFORMATION: Synthetic peptide with cycle on the side chains
      of Lys3 and Asp8

<400> SEQUENCE: 9

His Ala Lys Pro Gly Gly Ile Asp Pro Glu Gln
 1               5                  10

<210> SEQ ID NO 10
<211> LENGTH: 9
<212> TYPE: PRT
<213> ORGANISM: Artificial sequence
<220> FEATURE:
<223> OTHER INFORMATION: Synthetic peptide with cycle on the side chains
      of Lys2 and Asp4.

<400> SEQUENCE: 10

Gly Lys Phe Asp Ser Pro Glu His Gln
 1               5

<210> SEQ ID NO 11
<211> LENGTH: 11
<212> TYPE: PRT
<213> ORGANISM: Artificial sequence
<220> FEATURE:
<223> OTHER INFORMATION: Synthetic peptide with cycle on the side chains
      of Lys4 and Asp7.

<400> SEQUENCE: 11

Gly Gly Gly Lys Phe Trp Asp Ile Pro His His
 1               5                  10

<210> SEQ ID NO 12
<211> LENGTH: 10
<212> TYPE: PRT
<213> ORGANISM: Artificial sequence
<220> FEATURE:
<223> OTHER INFORMATION: Synthetic peptide with cycle on the side chains
      of de Lys2 and Asp5.

<400> SEQUENCE: 12

His Lys Gly Ile Asp Ser Pro Glu Gln His
 1               5                  10

<210> SEQ ID NO 13
<211> LENGTH: 10
<212> TYPE: PRT
<213> ORGANISM: Artificial sequence
<220> FEATURE:
<223> OTHER INFORMATION: Synthetic peptide with cycle on the side chains
      of Lys2 and Asp4.

<400> SEQUENCE: 13

Gly Lys Phe Asp Leu Ser Pro Glu His Gln
 1               5                  10
```

```
<210> SEQ ID NO 14
<211> LENGTH: 11
<212> TYPE: PRT
<213> ORGANISM: Artificial sequence
<220> FEATURE:
<223> OTHER INFORMATION: Synthetic peptide with cycle on the side chains
      of Asp2 and Lys6.

<400> SEQUENCE: 14

Gly Asp Ala Gly Ala Lys Leu Leu Ser Ser Arg
  1               5                  10

<210> SEQ ID NO 15
<211> LENGTH: 12
<212> TYPE: PRT
<213> ORGANISM: Artificial sequence
<220> FEATURE:
<223> OTHER INFORMATION: Synthetic peptide with cycle on the side chains
      of Glu3 and Lys7.

<400> SEQUENCE: 15

Gly Met Glu Ala Gly Ile Lys Leu Cys His Arg Gln
  1               5                  10

<210> SEQ ID NO 16
<211> LENGTH: 11
<212> TYPE: PRT
<213> ORGANISM: Artificial sequence
<220> FEATURE:
<223> OTHER INFORMATION: Synthetic peptide with cycle on the side chains
      of Glu2 and Lys5.

<400> SEQUENCE: 16

Gly Glu Gly Tyr Lys Leu Asp Glu Arg Ser Gln
  1               5                  10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide with cycle on the side chains
      of Glu3 and Lys6.

<400> SEQUENCE: 17

Gly Gly Glu Ala Gly Lys Leu Cys Pro Pro Arg Tyr
  1               5                  10

<210> SEQ ID NO 18
<211> LENGTH: 9
<212> TYPE: PRT
<213> ORGANISM: Artificial sequence
<220> FEATURE:
<223> OTHER INFORMATION: Synthetic peptide with cycle on the side chains
      of Glu3 and Lys5.

<400> SEQUENCE: 18

Gly Leu Glu Phe Lys Leu Leu His Gln
  1               5
```